(12) United States Patent
Baum et al.

(10) Patent No.: US 9,364,770 B2
(45) Date of Patent: Jun. 14, 2016

(54) BIODIESEL MANUFACTURING SYSTEM AND APPARATUS

(71) Applicant: The Biocube Corporation Ltd., Bundall (AU)

(72) Inventors: Laurence Baum, Balmain (AU); A Alexander Kelly, Nerang (AU)

(73) Assignee: The Biocube Corporation Ltd., Bundall, Queensland (AU)

( * ) Notice: Subject to any disclaimer, the term of this patent is extended or adjusted under 35 U.S.C. 154(b) by 0 days.

(21) Appl. No.: 13/818,649

(22) PCT Filed: Dec. 20, 2012

(86) PCT No.: PCT/AU2012/001567
§ 371 (c)(1),
(2) Date: Feb. 22, 2013

(87) PCT Pub. No.: WO2013/091002
PCT Pub. Date: Jun. 27, 2013

(65) Prior Publication Data
US 2014/0294693 A1    Oct. 2, 2014

(30) Foreign Application Priority Data
Dec. 20, 2011    (AU) ................................. 2011905329

(51) Int. Cl.
| | | |
|---|---|---|
| *B01J 19/18* | (2006.01) | |
| *B01F 5/14* | (2006.01) | |
| *C11C 3/10* | (2006.01) | |
| *B01D 3/00* | (2006.01) | |
| *B01J 19/00* | (2006.01) | |
| *C07C 67/03* | (2006.01) | |
| *C10L 1/02* | (2006.01) | |

(Continued)

(52) U.S. Cl.
CPC . *B01D 3/009* (2013.01); *B01F 5/14* (2013.01); *B01J 19/0066* (2013.01); *B01J 19/1806* (2013.01); *C07C 67/03* (2013.01); *C07C 67/08* (2013.01); *C07C 67/54* (2013.01); *C10L 1/026* (2013.01); *C11C 1/08* (2013.01); *C11C 3/003* (2013.01); *C11C 3/10* (2013.01); *Y02E 50/13* (2013.01); *Y02P 30/20* (2015.11)

(58) Field of Classification Search
CPC .................................. B01F 5/14; B01F 5/145
USPC ......................................................... 366/272
See application file for complete search history.

(56) References Cited

U.S. PATENT DOCUMENTS 4,164,506 A * 8/1979 Kawahara et al. ............ 554/167
6,286,988 B1   9/2001 Hasse
(Continued)

FOREIGN PATENT DOCUMENTS

BR    8802587 U2 *  8/2010
CA    2596578 A1 *  2/2009
(Continued)

OTHER PUBLICATIONS

International Search Report for International Application No. PCT/AU2012/001567 dated Apr. 3, 2013, 6 pages.

*Primary Examiner* — Jennifer A Leung
(74) *Attorney, Agent, or Firm* — Kilpatrick Townsend & Stockton LLP

(57) ABSTRACT

A portable biodiesel manufacturing or processing plant for processing on continuous basis a raw plant based oil feedstock to form biodiesel.

12 Claims, 29 Drawing Sheets

(51) Int. Cl.
  *C11C 1/08* (2006.01)
  *C11C 3/00* (2006.01)
  *C07C 67/08* (2006.01)
  *C07C 67/54* (2006.01)

(56) References Cited

U.S. PATENT DOCUMENTS

| | | | |
|---|---|---|---|
| 8,398,942 B2 * | 3/2013 | Brasil | 422/630 |
| 2003/0175182 A1 | 9/2003 | Teall et al. | |
| 2007/0056214 A1 * | 3/2007 | Bowen et al. | 44/629 |
| 2007/0175092 A1 * | 8/2007 | Ames | 44/629 |
| 2009/0277077 A1 * | 11/2009 | Gleason et al. | 44/388 |

FOREIGN PATENT DOCUMENTS

| | | | | |
|---|---|---|---|---|
| EP | 1061120 A1 * | 12/2000 | | |
| EP | 2090644 A1 * | 8/2009 | | C11C 3/10 |
| GB | 1081711 A | 8/1967 | | |
| WO | WO 2007069298 A1 * | 6/2007 | | |
| WO | 2009/089591 A1 | 7/2009 | | |
| WO | 2010/093670 A1 | 8/2010 | | |
| WO | WO 2010093670 A1 * | 8/2010 | | |

* cited by examiner

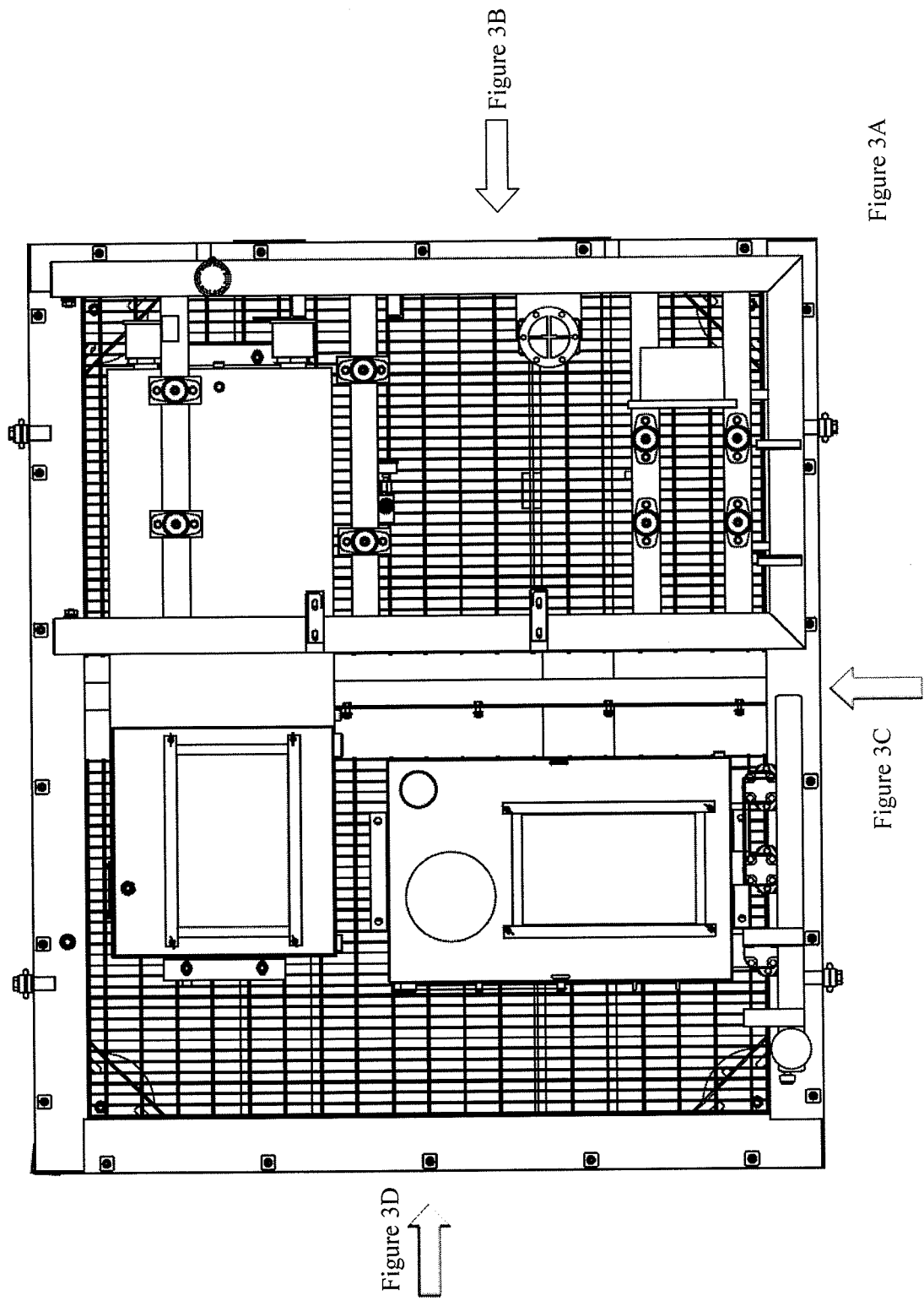

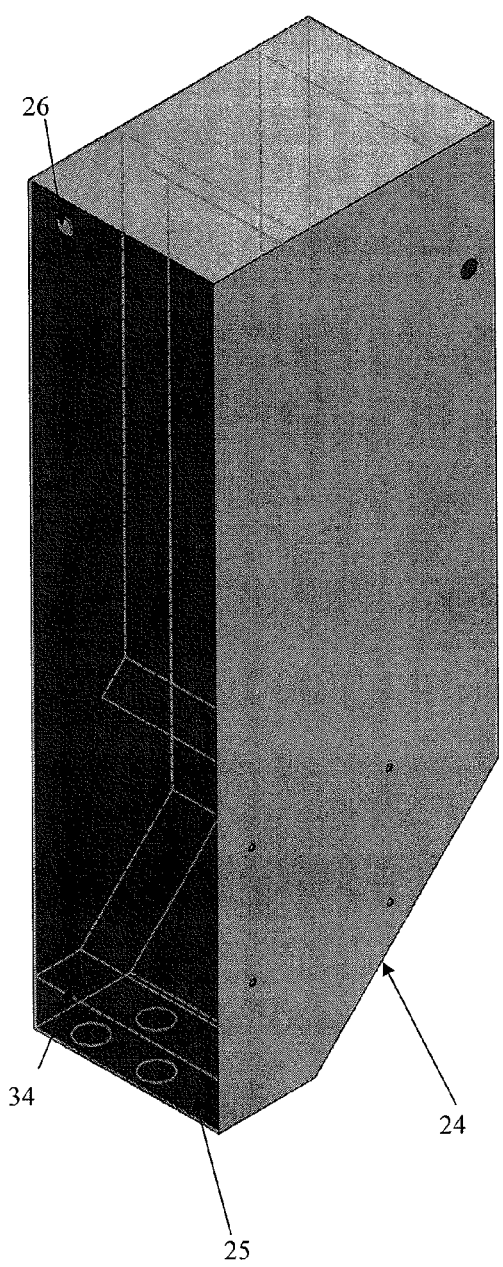
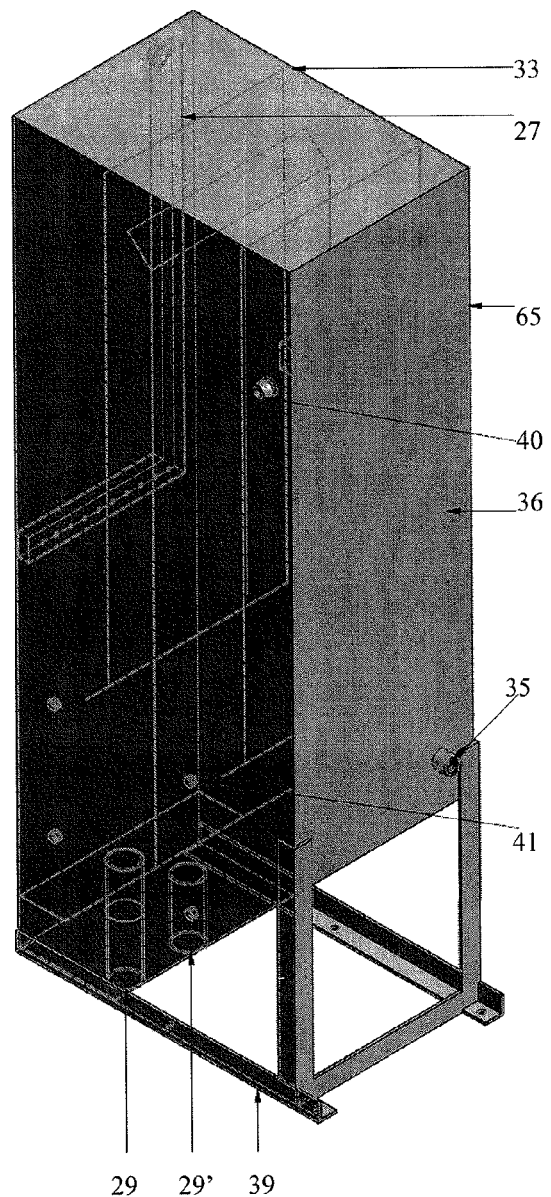
Figure 31
Figure 32

Figuer 32B

BIODIESEL MANUFACTURING SYSTEM AND APPARATUS

This application is the U.S. National Phase entry under 35 U.S.C. §371 and claims the benefit of International Application No. PCT/AU2012/001567, filed Dec. 20, 2012, which claims the benefit of Australian Patent Application No. 2011905329, filed Dec. 20, 2011, all of which are incorporated herein by reference in their entirety for all purposes.

FIELD OF THE INVENTION

The present invention relates to alternative and sustainable fuel sources and particularly to a system and apparatus for the production of biodiesel.

BACKGROUND ART

Biodiesel refers to a diesel-equivalent processed fuel consisting of short chain alkyl (methyl or ethyl) esters, made by transesterification of vegetable oils or animal fats, which can be used (alone, or blended with conventional diesel fuel) in unmodified diesel-engine vehicles.

On Aug. 31, 1937, G. Chavanne of the University of Brussels (Belgium) was granted a patent for a 'Procedure for the transformation of vegetable oils for their uses as fuels' (fr. 'Procédé de Transformation d'Huiles Végétales en Vue de Leur Utilisation comme Carburants') Belgian Patent 422, 877. This patent described the alcoholysis (often referred to as transesterification) of vegetable oils using ethanol (and mentions methanol) in order to separate the fatty acids from the glycerol by replacing the glycerol with short linear alcohols. This appears to be the first account of the production of what is known as 'biodiesel' today.

The common international standard for biodiesel is EN 14214.

There are additional national specifications. ASTM D 6751 is the most common standard referenced in the United States and Canada. In Germany, the requirements for biodiesel are fixed in the DIN EN 14214 standard and in the UK the requirements for biodiesel is fixed in the BS EN 14214 standard, although these last two standards are essentially the same as EN 14214 and are just prefixed with the respective national standards institution codes.

There are standards for three different varieties of biodiesel, which are made of different oils:
  RME (rapeseed methyl ester, according to DIN E 51606)
  PME (vegetable methyl ester, purely vegetable products, according to DIN E 51606)
  FME (fat methyl ester, vegetable and animal products, according to DIN V 51606)

The standards ensure that the following important factors in the fuel production process are satisfied:
  Complete reaction.
  Removal of glycerin.
  Removal of catalyst.
  Removal of alcohol.
  Absence of free fatty acids.
  Low sulfur content.

Whilst the conventional methods and apparatus for the production of biodiesel are adequate, they are typically large, on grid, complex, fixed chemical processing facilities, requiring a large number of staff to operate the facility and also transport costs and like to move the biodiesel to the end user. Alternatively, on a smaller scale they are batch processors that require on grid or external energy input and in infrastructure to house the system.

It will be clearly understood that, if a prior art publication is referred to herein, this reference does not constitute an admission that the publication forms part of the common general knowledge in the art in Australia or in any other country.

SUMMARY OF THE INVENTION

The present invention is directed to an independently powered, portable biodiesel manufacturing/processing system and apparatus, which may at least partially overcome at least one of the abovementioned disadvantages or provide the consumer with a useful or commercial choice.

With the foregoing in view, the present invention in one form, resides broadly in a biodiesel manufacturing or processing plant for processing on continuous basis a process fluid from a raw oil feedstock, the plant including
1. a housing containing a power generation means,
2. an inlet for raw oil from an oil bearing crop,
3. a raw oil heating vessel,
4. an esterification subprocess including a reactor in which the process fluid is reacted with alcohol via selective esterification by a catalyst
5. a trans-esterification subprocess including an alkali dosing mechanism to dose the process fluid in the presence of an alcohol, a powered sheer mixer to mix the alkali, alcohol and process fluid, and a heated cauldron for primary separation of glycerol from the process fluid,
6. a flash evaporation separator for separation of excess alcohol from the process fluid through a differential pressure vaporisation process, and
7. one or more finishing processes.

In an alternative form, the invention resides in a biodiesel manufacturing or processing plant for processing on continuous basis a process fluid from a raw oil feedstock, the plant including
1. a housing containing a power generation means,
2. an inlet for raw oil from an oil bearing crop,
3. a raw oil heating vessel,
4. an esterification and trans-esterification process including a reactor in which the process fluid is reacted with alcohol via selective esterification by a catalyst
5. a powered sheer mixer to mix the alkali, alcohol and process fluid, and a heated raw oil tank
6. a combined reactor and primary separation/settling tank for the removal of glycerol from the process fluid,
7. a pre-heater and vacuum tank for separation of excess alcohol from the process fluid through drawing of a vacuum over the hot fluid and vaporisation process, and
8. one or more finishing processes.

In a further alternative form, the invention resides in a biodiesel manufacturing or processing plant for processing on continuous basis a process fluid from a raw oil feedstock, the plant including
1. a housing containing a power generation means,
2. an inlet for raw oil from an oil bearing plant crop or waste plant based oil
3. a raw oil heating vessel,
4. a powered sheer mixer to mix triglycerides from the raw oil, and at least one reactant alcohol according to a transesterification process,
5. a combined reactor and primary separation/settling tank for the reaction of the triglycerides and at least one alcohol to produce at least one fatty acid ester and at least one alcohol;

6. a heater and vacuum separator for separation of the at least one alcohol from the at least one fatty acid ester through drawing of a vacuum over the hot fluid and vaporisation process, and
7. one or more finishing processes.

The powered shear mixer may provide a high-energetic shear zone to allow the transesterification reaction to begin to take place in the mixer by reducing the droplet size of the immiscible liquids such as oil or fats and methanol. Therefore, the smaller the droplet size the larger the surface area the faster the catalyst can react.

An alternative, catalyst-free method for transesterification may use raw oil and a supercritical alcohol, normally methanol at high temperatures and pressures in a continuous process. In the supercritical state, the oil and alcohol are usually in a single phase, and the reaction occurs spontaneously and rapidly. The process can tolerate only small amounts of water in the feedstock, free fatty acids are converted to methyl esters instead of soap. A wide variety of feedstocks can be used. Also the catalyst removal step can be reduced or eliminated. High temperatures and pressures are required, but energy costs of production are similar or less than catalytic production routes.

The manufacturing plant of the present invention can take in most oil-bearing crops—jatropha, palm, rapeseed, and the like—and process it to produce biodiesel fuel to the required European/North American Standard. This means that the output of the plant can go straight into the tank of any diesel engine without modifying its settings. The process undertaken will typically be alcoholysis (often referred to as transesterification).

The output at approximately 250 liters per hour in a continuous flow is ideal for smaller communities which want to use the fuel themselves. It is particularly useful for communities that have little or no 'on' grid power or alternative energy source to operate the plant.

The housing will preferably be a bespoke plastic container surrounding a frame to which one or more components of the plant. The container will typically be divided into at least a pair of compartments in order to house particular components of the manufacturing plant and preferably, a pair of approximately equal sized compartments. In particular, one end of the housing preferably contains the power generation means and the other end of the housing has the process equipment. For operational safety, a bulk head wall will normally be provided within the housing to divide the two compartments.

In order to provide adequate ventilation a grated floor and openings should be provided in the base wall or a lower portion of the sidewalls in order to allow the inadvertent escape of heavier than air gases. The housing is preferably also provided with lateral openings and events in upper regions in order to allow the escape of lighter than air gases. Notwithstanding the ventilation, the container will normally be spaced above the ground surface or mount surface to promote natural flow under the container and circulation within the process area within the container.

Auxiliary circulation promotion means is provided in the form of a fan mounted to the power generation system.

The container will normally be provided with lifting/securing/transport points or connections. These connections will preferably be accessible only from within the container, and therefore access into the interior of the container will usually be required before the container can be secured in position, or removed.

Lift points will normally be provided at at least some of the lower corners of the container, normally at each of the four lower corners adjacent each corner such that at least two points are provided on each side of the container.

As stated above, the container is preferably mounted above ground level. Normally, the container will be mounted on a plurality of legs. A particularly preferred height will be 450 mm above the ground or mount surface. It is preferred that the legs used to mount the container are adjustable to allow for height adjustment of the container and also to provide levelling capabilities.

The container and/or the legs of the container will normally be mounted relative to a plinth or slab laid on the ground surface. The slab will preferably be or include concrete and will normally be reinforced.

The container may be mounted utilising sound and/or vibration absorbing material. There will normally be at least one access door to the interior of the container. It is preferred that the access door will have an at least partially clear portion in order that a user may be able to view interior of the container without opening the access door. It is further preferred that when sealed, the access door will not allow the ingress or egress of gases.

The housing will typically include a platform relative to which the components of the plant are mounted. Normally, the shape of the platform will be defined by a rigid frame made of a plurality of frame members. The frame will typically be generally rectangular.

Each frame member will preferably be rigid and strong and for this reason, a metal is preferred. Each frame member will also probably be substantially hollow. According to a preferred embodiment, the frame members used will not only function to support the platform to which the components of the plant are mounted, but will also typically be used to store working fluids such as hydraulic oils and diesel for the engine. Therefore, the frame members may be linked to one another to form a storage tank. Any fluid may be stored in the frame tank.

The platform will typically take the form of a substantially planar member attached to the frame. The platform may be a solid member or alternatively, a rigid grate or mesh may be used as this may increase airflow through the plant during operation.

The housing will typically be provided with one or more walls in order to enclose the plant. It is preferred that a number of openings are provided in one or more walls of the housing. It is preferred that these openings can be closed or sealed by doors or other movable members. During operation, the doors or movable members will normally be opened again to promote airflow through the plant them but the doors or movable members will normally be closed or sealed for transport and prior to location onsite. The doors or movable members can also be closed when the plant is not in operation in order to secure the plant against local wildlife or potentially against vandals. According to a particularly preferred embodiment, a pair of doors are provided in each of the end walls (the end walls being located adjacent either the power generation means or the process equipment).

The walls and doors or movable members will typically be formed from a plastic but materials such as light metal, provided it is sufficiently rigid and strong, could be used in the alternative.

The plant of the present invention includes a power generation means, and the power generation means will normally be mounted towards one end of the container.

The power generation means will normally include a diesel generating set power pack. Typically, the power generation means will produce hydraulic power and electricity through a direct drive or alternatively a hydraulic drive which will then be used to power the other process components. The power generation means is preferably located within a separate compartment within the container and may be fully enclosed. This may assist with limiting contamination of the process and/or the raw oil or finished biodiesel.

The power generation means will typically run on biodiesel produced by the plant. An initial charge of diesel fuel may be provided after which a portion of the production biodiesel will usually be used. Indeed the production of biodiesel from the plant may be a net production after accounting for the biodiesel used to power the power generation means.

The power generation means will normally, by its very nature, produce heat during operation. Waste heat from the power generation means may preferably be used to partially heat the raw oil or to provide heat to other process equipment.

The power generation means is normally associated with a pump in order to move the raw oil, intermediate products and finished biodiesel into, out of and through the process steps.

The raw oil is heated in a raw oil-heating vessel with three phase heaters fitted. The heaters will preferably supply enough energy to the oil to raise the raw oil temperature to approximately 110° C.

The plant of the present invention may further include an esterification sub-process including a resin based dosing mechanism to dose the process fluid in the presence of an alcohol and an esterification settling tank. Suitable process equipment is provided in the plant to facilitate this sub process.

If the process fluid is to be subjected to the esterification sub process, it will typically undergo esterification after primary heating. One or more filters may be used to filter the raw oil heater prior to heating in the preferred hot oil tank, after heating in the hot oil tank or alternatively, filtration may take place on each side of the hot oil tank.

The esterification sub process will normally involve reacting a mixture of free fatty acids, either as neat or in the corresponding oil process fluid being with alcohol via selective esterification by a catalyst that selectively esterifies the desired free fatty acid(s).

A "reaction zone" can be a flow reactor or a portion of a flow reactor. When a single flow reactor is used, the zones are divided from each other by points along the reactor at which water is separated from the reaction mixture. When multiple reactors are used, with separation of water between reactors, typically each reactor is a reaction zone. Suitable reactors include, e.g., packed-bed reactors, continuous stirred tank reactors, column reactors, etc. A reaction zone may encompass multiple stages in a column reactor. Preferably, reactors are configured as co-current flow reactors, i.e., the fatty acid and alcohol pass through the reactor in the same direction.

Typically, the product stream from the esterification process is sent to a transesterification process, where it is contacted with a transesterification catalyst and an alcohol, preferably after separating water in a tank.

Typically, the reaction is carried out in a flow reactor, and preferably the contact time is at least 60 minutes, alternatively at least 100 minutes. Preferably, the contact time is no more than 6 hours, alternatively no more than 4 hours, alternatively no more than 2 hours.

The residence time in the esterification system typically will be dependent upon required production output and will typically be determined according to the maximum production output. It may also be dependent upon the particular raw oil feedstock.

Preferably the catalyst is a gel-type acidic ion exchange resin having 0.25 wt % to 2.75 wt % crosslinker, and having sulfonic acid functionality. The reaction mixture is preferably in contact with the catalyst in a continuous reactor in a temperature range from 40° C. to 120° C. for at least 15 minutes.

The location of the reactor is within the process side of the container.

The preferred esterification tank is a column tank and normally more than one is provided. The column may be a packed column or not.

The alcohol used will preferably be methanol or ethanol or another alcohol could be used in the esterification sub process.

The esterification sub process equipment will be provided in the plant of the present invention but the process may not be included in the process, dependent upon the feedstock used and in particular, the acid number of the raw oil feedstock. Therefore, whilst the esterification sub process equipment will be present in the plant, a bypass may be provided once the heating of the raw oil has been achieved. The bypass will typically connect more or less directly to the trans-esterification sub process. Typically however the esterification sub process may be used, at least to some extent, for most types of raw oil feedstock.

Further, a pump will normally be provided in order to dose the acid and/or the alcohol into the process fluid.

The plant of the present invention includes a trans-esterification sub process to dose the process fluid in the presence of an alcohol and a reactor tank which is associated with and preferably sits at least partially within the raw oil heating tank which acts as a heat exchanger, for primary separation of glycerol from the process fluid. Suitable process equipment is provided in the plant to facilitate this subprocess.

The process fluid is subjected to a trans-esterification sub process in order to form the preferred fatty acid methyl ester (FAME). The trans-esterification sub process will normally be after esterification or if the raw oil does not require esterification as a pre-treatment, after primary heating.

The trans-esterification sub process will normally involve the process fluid being heated and dosed with an alkali in the presence of alcohol. Accordingly, the alkali is preferably used as a catalyst in the trans-esterification process. The alkali dosed process fluid will normally proceed to a trans-esterification to a heated settling tank, or reactor tank. The residence time in the trans-esterification settling tank will be dependent upon required production output and the size of the settling tank will typically be determined according to the maximum production output and required residence time. It may also be dependent upon the particular raw oil feedstock.

The alcohol used will preferably be methanol or ethanol or another alcohol could be used in the trans-esterification sub process.

The mixing or dosing of the process fluid with the alkali in the presence of an alcohol may take place in line (turbulent fluid mixing device) but preferably, a mixing vessel will be provided in order to ensure a consistent mix.

Further, two pumps will normally be provided in order to dose the alkali and the alcohol into the process fluid.

The preferred alkali is sodium or potassium hydroxide and methanol or ethanol as the reagent. A preferred mixture is known as sodium (or potassium) methylate (or ethylate).

A mixer is typically provided in order to mix the process fluid, the alcohol and the catalyst. According to a particularly preferred embodiment, the mixer is made of a heat resistant plastic and contains a series of sheer plane gears that are driven at speed through a hydraulic drive. The heat process fluid or oil is injected at the top, the alcohol and catalyst through the upper side of the mixer. All three liquids then coalesce and pass down and through the rotating gears which agitate the fluids mixing them together and causing the reaction to commence. The mixed fluid is then fed into the reactor tank which fills up. As it does so the glycerine settles to the bottom of the tank. In this form, the mixer also functions as a reactor vessel.

In one form, the mixer includes an outer housing having a central longitudinal axis, at least two interengaging, counter-rotating toothed mixing bodies, the toothed mixing bodies each rotating about a central axis, the respective axes offset radially and spaced along the central longitudinal axis of the outer housing.

Preferably, the mixer will include at least three mixing bodies, the central axis of each mixing body being offset at approximately 120° from each of the other central axes. Normally, the central axes of the mixing bodies will be aligned in a triangular configuration when viewed along the central longitudinal axis of the housing.

In an alternative form, the invention resides in a mixer including an outer housing having a central longitudinal axis, and at least a pair of end portions, each end portion having at least one toothed mixing body associated therewith, the toothed mixing bodies of the respective end portions interengaging and counter-rotating about a central axis, the respective axes offset radially and spaced along the central longitudinal axis of the outer housing.

In a further alternative form, the invention resides in a mixer including an outer housing having a central longitudinal axis, at least a pair of end portions and at least one intermediate portion, each portion having at least one toothed mixing body associated therewith, the toothed mixing bodies of the respective portions interengaging and counter-rotating about a central axis, the respective axes offset radially and spaced along the central longitudinal axis of the outer housing.

The mixer of the present invention has an outer housing. The outer housing may be solid or hollow, preferably made of plastic. For example, the outer housing may include an outer sleeve which is substantially tubular with one or more removable body portions located within the outer sleeve. Alternatively, the housing may be a solid portion or portions with at least one opening therein to define a mixing cavity.

Preferably the mixer is a continuous mixer as opposed to a batch mixer although it may be operated in a batch mode.

The housing is typically modular in nature with a number of portions being attached together to form the mixer, with the number of portions and their particular configuration chosen according to the application.

Preferably, where provided in the sleeved configuration, the body portions are shaped and sized to fit within the sleeve. Typically, tight tolerances are used in order to prevent leakage between the sleeve and the body portions. Seals may be used. Seals may also be used when the mixer is formed of solid bodies but it that case, the seals will typically be between adjacent solid bodies.

Typically, the body portions mount the mixing bodies. Normally, the body portions are basically solid portions with a number of openings therein to at least partially receive the mixing bodies.

Each of the body portions, whether intermediate or end portions, will typically have at least one circumferential, transversely extending flange with a number of openings there through in order to receive elongate fasteners to attach the portions to each other. Each intermediate portion will typically have a pair of transversely extending flanges, one at either end, and each end portion will typically have a single transversely extending flange.

Where the portions are solid, the openings will normally be formed through the solid portions outside of the mixing cavity.

The housing and/or body portions are preferably fixed together using elongate fasteners extending substantially parallel to the longitudinal axis of the housing. Normally, these elongate fasteners will be threaded rods and using the rods, a compressive force may be applied to the housing and/or body portions to seal the respective housing and/or body portions together.

Preferably, the body portions are stepped portions. Normally, the number of steps in each body portions equals the number of mixing bodies which the body portion mounts.

Typically, the housing will be cylindrical and therefore, the body portions will be substantially cylindrical as well. However, the housing may have any shape and indeed, individual body portions may have any shape. Preferably, each of the body portions will mount a number of mixing bodies in relation thereto.

The body portions of the preferred embodiment will typically include a pair of end portions and at least one intermediate portion.

The end portions are typically configured as a top and a bottom end portion as the mixer will typically be used in a substantially vertical orientation (but it need not be). One or both of the end portions will typically be associated with drive means to drive at least one of the mixing bodies. Because the mixing bodies in the mixer inter-engage with one another, driving one of the mixing bodies will typically cause sympathetic rotation of the other mixing bodies. One example of drive means, which may be used, is a driveshaft associated with a bevelled or mitred gear to mesh with at least one of the mixing bodies associated with one of the end portions. Each of the end portions may have an associated drive means in order to provide drive force from either end of the mixer.

Alternatively, one or more drive means may be provided in association with one or more intermediate portions in order to reduce the strain on the furthest mixing bodies.

Typically, the drive means will include a driveshaft which extends into the housing substantially perpendicularly to the main longitudinal axis of the housing, whether through the end portions or one or more intermediate portions.

One of the end portions will typically have at least one inlet. There may be more than one inlet provided. Further, at least one primary inlet for process fluid will be provided and at least one secondary inlet will be provided for catalyst and/or alcohol.

Normally, a single primary inlet is provided approximately centrally in the upper end portion. A pair of secondary inlets are provided perpendicularly to the primary inlet and offset from each other radially about the upper end portion.

Normally, the secondary inlets will provide material directly onto at least one mixing body. Preferably, each secondary inlet may be a conduit which extends perpendicularly to the central longitudinal axis of the housing through the end portion, which will typically be at least partially solid.

The inner end opening of each secondary inlet will typically be shaped in order to correspond with the shape of a mixing body. In this way, the end of each secondary inlet may closely match the shape of the mixing body to spread the material introduced into the mixer over the mixing body.

One of the end portions, normally the one opposite the end portion having the inlets, will be provided with at least one outlet. Typically, the top end portion will have the inlets and the bottom end portion at least one outlet. In this way, the material may move through the mixer using the force of gravity, as well as being forced through the mixer by the rotation of the mixing bodies. Normally the outlet will be located approximately centrally in the lower end portion.

Each of the end portions will typically be configured to receive and locate at least one, and typically a plurality of mixing bodies. Each end portion will therefore have an outer side and an inner side. The inner side of the end portion will typically have a stepped configuration where configured to receive multiple mixing bodies, with the number of steps equaling the number of mixing bodies.

According to a particularly preferred embodiment, where an end body portion mounts three mixing bodies, the body portion will have three steps at different levels on the inner wall. In this particularly preferred embodiment, each end of each body portion will therefore be divided into three steps, with each step be approximately 120° of arc.

Normally, there will be a shaped opening in each step to at least partially receive and locate each mixing body. Normally, each opening in each step will receive half of height of the mixing body. Normally, the inlet to the top end body will be located above the topmost mixing body of the mixer.

According to a preferred configuration, each end portion has three steps, each configured as a 120° arc portion, one of the 120° steps being a depression, and one being a 120° upstand.

There will typically be a main opening and a pair of side openings with the side openings receiving laterally extending axles provided on the mixing body and about which the mixing body will rotate. The main opening will preferably receive the toothed portion of the mixing body.

Bearings or low friction liners may be provided in association with each of the side openings in order to reduce the amount of wear in the openings or to reduce the force required to rotate the mixing bodies.

Preferably, the main openings in the intermediate portions will define a circuitous path through which material can move under force provided by the mixing bodies through the mixer from inlet to outlet.

It is preferred that the main openings are closely shaped to correspond to the shape of the mixing bodies in order to allow rotation of the mixing bodies within the openings but to limit all other movement. The toothed portion of the mixing body will typically have a tight tolerance with a wall defining the main opening in the end portions.

As mentioned above, a preferred form mixer includes at least two end portions and at least one intermediate portion. Where provided, each intermediate portion will preferably have two end surfaces and each of the end surfaces will, according to the particularly preferred cylindrical embodiment of the mixer, be substantially circular.

Each of the two end surfaces will typically be divided into a number of stepped portions according to the number of mixing bodies included in the mixer. However, in the most preferred form, each end surface will have three steps. Typically, mixing bodies will be mounted between the end surfaces of the intermediate portion and the inner wall of the end portion. Further, mixing bodies will be mounted between adjacent end surfaces of adjacent intermediate portions.

Again, according to the particularly preferred embodiment, typically three mixing bodies will be "sandwiched" between the end walls of adjacent body portions. Therefore, each intermediate portion will typically mount six mixing bodies or two pairs of three mixing bodies (one pair of three located at each end wall) according to the particularly preferred embodiment.

Each intermediate portion will typically mount at least two, and normally three mixing bodies between an intermediate portion and either an adjacent intermediate portion or an end portion.

Therefore, alternative preferred embodiments will have the following configurations and numbers of mixing bodies:

| Configuration | No. of Mixing Bodies |
| --- | --- |
| Two end portions | Three |
| Two end portions and one intermediate portion | Six |
| Two end portions and two intermediate portions | Nine |

Each of the mixing bodies will be substantially circular in configuration. As mentioned above, each of the bodies will have at least one and typically a pair of axle portions extending from each side of a central toothed portion.

Each of the mixing bodies will preferably be configured or shaped as a double mitre gear. Bevelled gears may be used, but mitre gears are preferred due to the fact that intermeshing mitre gears have the same number of teeth whereas bevelled gears are used to change speed and therefore adjacent gears may have different numbers of teeth. According to the present invention, mitred gears are preferred but one or more bevelled gears may be used.

When viewed from the side, each mixing body will typically have an axle portion extending from either lateral side of a substantially hexagonal shaped central toothed portion. The axle portions will typically extend from a substantially circular sidewall. The other walls of the hexagonal shaped central toothed portion will typically be provided with a plurality of teeth.

These walls will typically be frustoconical in shape with the larger diameter portions located back to pack to form a circumferential ridge about the middle of the mixing body.

The angle of the mitre will typically differ according to the number of mixing bodies included in the mixer. However, according to the preferred 120° offset configuration, each of the mitre gear shaped mixing bodies will have will have a pair of toothed surfaces extending circumferentially around the mitre gear shaped mixing body, each of the toothed surfaces extending at an angle of approximately 30° to the axis of rotation of the mixing body.

The teeth may have any shape and/or configuration. For example, the teeth provided may have a straight or spiral configuration. The mixing bodies of the preferred embodiment will typically have a low ratio in order to convert the majority of the force into mixing force. Further, the teeth may have any shape such as straight, or coniflex, with the shape of the teeth chosen to maximise the particular form of mixing which is desired.

Lubrication of the inter-engaged mixing bodies will typically occur by the material which is being mixed.

In a particularly preferred configuration wherein each intermediate portion mounts six mixing bodies, the central axis of each mixing body will preferably be offset at approximately 120° from each of the other central axes. Normally, the central axes of the mixing bodies will be aligned in a triangular configuration when viewed along the central longitudinal axis of the housing.

Typically, the central axes of respective mixing bodies are spaced along the length of the central longitudinal axis of the housing in a repeating pattern.

The central axes of adjacent mixing bodies of adjacent portions will preferably be offset from one another.

The mixer will typically have an associated speed regulation system in order to control the speed of the mixing bodies.

The particular shape in configuration of the mixing bodies will typically be chosen to optimise the horsepower or torque to be transmitted during the mixing, the speed of the mixing bodies and the duty cycle of the mixer.

Portions of the mixer of the present invention may be manufactured from different materials. For example, the body portions and outer housing may be metal with the mixing bodies being either metal or composite or plastic. Of course, the materials used will depend upon the materials being mixed.

The mixer of the present invention is particularly well adapted to mix highly viscous liquid components, solids or pastes. It provides a shearing and/or kneading action designed to disrupt attractive forces between particles of each component to be mixed, breaking the bulk components into smaller particles by disrupting the macroscopic forces binding the component particles to one another to enhance the mixing. The mixer of the present invention also utilises the shearing and/or kneading action to force particles or physically squash the particles of two or more components together.

The reactor tank is located after the alkali mixing process in order to achieve primary separation of the glycerol from the FAME by settling. The reactor tank is preferably within the raw oil tank which acts as a heat exchanger and will normally be a substantially rectangular process vessel with a tapered lower portion to allow the heavier fluid to be drawn off from a lower portion of the reactor tank. There will normally be an inlet in the upper portion for the process fluid to be separated. At least one, and preferably multiple outlets are provided spaced across the width of the lower portion of the reactor tank. The internal volume of the reactor tank may be provided with one or more internal baffles or separating parts.

The plant of the present invention includes a secondary heater and vacuum tower for separation of excess alcohol from the process fluid through vaporisation under vacuum. In operation, a fluid having at least one volatile component mixed therein enters through flows from the top of the sealed reactor tank into the secondary heater generally including a tube and a heating element. The secondary heater is preferably located beneath the engine and above the raw oil tank. Once flooded the re-heated fluid is fed continuously into the vacuum tower, which is located on the process side of the plant. A vacuum is preferably drawn throughout the tower. Vapour is removed from the vacuum tower through the vacuum pump and overboard where it is preferably condensed at atmospheric pressure and stored externally to the plant. The fluid preferably flows over a series of dish-like trays stacked vertically within the tower. The fluid is then collected and pumped out of the bottom of the tower.

Alternatively, a chantrelle can be used as a separator including a substantially bell-shaped inner module having a crown, waist, separation surface and lip with a mixture inlet extending upwardly through the crown and an outer hood containing the inner module and having at least one vapour outlet opening therein, the inner module mounted for rotation within the hood.

In operation, a fluid having at least one volatile component mixed therein enters through the mixture inlet and flows over the inner module during rotation. Due to the shape of the inner module, the cross-sectional area of the separation surface and lip portions are approximately 100 times that of the inlet and the inlet flow is adjusted such that the thickness of the mixture on the inner module reduces as it flows downwardly across the surface of the inner module.

A close fitting hood is fitted, through which air is preferably drawn with a stimulated flow. Due to the shape of the inner module and/or the hood, the airflow preferably travels around the surface of the inner module, in a helical pattern. As the air rises through the air space between the inner module and the hood, its velocity increases, and the pressure differential across the surface increases, permitting the more volatile components of the mixture to escape the surface tension of the mixture and be carried off in the airflow, whilst the less volatile component(s) of the fluid flow down the inner module and off the lip to be collected below.

Without wishing to be limited by theory, the principle of operation is a combination of Bernoulli's Principle and Flash Evaporation. The degree of separation will be affected mainly by the relative volatilities of the components, including the differing boiling points of components entrained within the fatty acid methyl ester FAME, the inlet flow rate, the rotation speed of the inner module and the flow rate of the air through the air space.

The separator of the present invention finds particular application in a biodiesel manufacturing process to separate methanol from the FAME. The temperature of the FAME is preferably approximately 65° C. at the point of entry. The FAME passes through the separator and is collected in a chamber under the inner module. The alcohol is exhausted through the outlet where it passes over a condenser and re-captured or exhausted through a charcoal based filter and released to atmosphere.

The substantially bell-shaped inner module will typically be hollow. It will further be substantially circular in cross-section, although the dimension of the circular cross-section will typically change over the height of the module, narrowing towards the crown of the inner module.

The mixture inlet will typically be substantially centrally located through the bell-shaped inner module. The mixture inlet will typically extend over the height of the inner module from a plane adjacent or at the lip of the inner module and through the crown of the inner module.

The crown of the inner module will preferably be arcuate, curving from the inlet to an upper shoulder.

A lower portion of the inner module will typically be thicker as will an upper portion of the inner module. Typically, the lower portion of the inner module will preferably extend from the waist of the inner portion, through the separation surface portion and to the lip. The lower portion of the inner module may be shaped in this manner to provide weight distribution towards the lower side of the inner portion as this may improve stability during rotation.

An upper portion of the inner module will typically be thicker as well. Normally, the upper portion will extend from an upper section of the waist, across the shoulder to the crown. The upper portion of the inner module may be substantially solid except for the mixture inlet.

The inner module may be manufactured of any material suitable to withstand what may be a harsh environment depending upon the mixture which the separator is used to separate. Typically, the inner module will be manufactured of metal, plastic or composite material.

The inner module use typically mounted for rotation about a central axis which is typically coaxial with a central axis of the mixture inlet. Preferably, the tubular inlet may be used as a mounting in order to rotate the inner module. Rotation may be achieved using any mechanism or drive means to achieve the rotation.

The separator of the present invention also includes an outer hood containing the inner module and having at least one vapour outlet opening therein. The outer hood is preferably shaped to correspond to the shape of the inner module. In particular, an inner surface of the outer hood is preferably shaped to correspond to an outer shape of the inner module.

The inner surface of the outer hood is preferably spaced from the outer surface of the inner module over its height. The separation distance between the inner surface of the outer hood and the outer surface of the inner module may change over the height of separator. Preferably, the separation distance is larger at an upper portion of the separator than at a lower portion of the separator. The separation distance may increase from the lower portion to the upper portion.

It is also preferred that the crown of the inner module is separated from the crown of the outer hood.

The outer hood is preferably generally frustoconical in shape with an open bottom and a crown.

Typically, the at least one vapour outlet is through the crown of the outer hood. According to a particularly preferred embodiment, a single vapour outlet is provided approximately centrally across the crown of the outer hood and most preferred is that the vapour outlet is directly over the mixture inlet of the inner module. The alcohol vapour is exhausted through the outlet where it passes over a condenser and re-captured or exhausted through a charcoal based filter and released to atmosphere.

The outer hood will typically have a side wall which is thicker through the waist then the portions at the crown, adjacent the side bow of the inner module and at the lip.

Preferably, when the inner module is fitted within the outer hood, an annular opening is defined between the lip of the inner module and the lip of the hood at a lower end of the separator. Liquid may exit through this annular opening and the annular opening will also allow gas, preferably air, to enter the separator in a direction opposite or substantially opposite to that of the mixture flow.

There will preferably be an additional settling tank located in the process flow after the chantrelle. This settling tank may be used for further separation of the FAME or bio diesel from other components remaining in the process flow.

There may also be one or more filters located after the vacuum tower and or chantrelle in order to provide the bio diesel in as clean a form as is possible for the use. At least one cellulose filter and at least one polishing filter are preferred.

One more pumps may be provided in association with the finished bio diesel flow in order to move the bio diesel to its required location.

As stated above, glycerol is released in the chemical reaction, and has to be collected. The amount of glycerol collected is broadly in line with the concentration of catalyst, but in general terms, will be approximately 12% of the net FAME output. The glycerol produced by the plant of the preferred embodiment is typically contaminated with soaps, excess catalyst, methanol and other contaminants. The glycerol has a number of uses ranging from a source of heat if burned at temperatures in excess of 350° Celsius.

The glycerol is primarily settled out of the FAME in the reactor tank and again in the settling tank and the polishing filter. Additional extraction of impurities takes place in the filter between the delivery pump and the polishing filter. The reactor tank and the polishing filter should have the collected glycerol drained every hour, or thereabouts.

The feedstock used according to the present invention can include most oil bearing fruit or plants. Examples include:

| | | |
|---|---|---|
| corn (maize) | cashew nut | oats |
| lupine | kenaf | calendul |
| cotton | hemp | soybean |
| coffee | linseed (flax) | hazelnut |
| euphorbia | pumpkin seed | coriander |
| mustard seed | camelina | sesame |
| safflower | rice | tung oil tree |
| sunflower | cocoa (cacao) | peanut |
| opium poppy | rapeseed | olive |
| castor bean | pecan nuts | jojoba |
| jatropha | macadamia | brazil nut |
| avocado | coconut | oil palm |

Other feedstocks can be used with an appropriate adjustment of the process conditions or parameters.

The process of making FAME is a chemical reaction that removes a glycerol molecule that ties together carbon and hydrogen atoms in fatty acid chains and replaces the broken bond with an alcohol (methanol) molecule on each chain. Three chains bonded by a single glycerol molecule are triglycerides. As the oil ages, it oxidises or deteriorates, and the number of triglyceride chains that break down result in an increase of Free Fatty Acid (FFA) chains. Indeed, some crops have characteristically high Free Fatty Acid chains, such as olive oil. FFA is measured as a percentage that is called the Acid Number. Oils with high Acid Numbers require a pre-treatment, called esterification.

The process of esterification uses a acid resin as a catalyst and methanol (or ethanol) as the reagent. Transesterification, on the other hand, uses an alkaline catalyst (sodium or potassium hydroxide) mixed with methanol (or ethanol) as the reagent and is known as Sodium (or Potassium) Methylate (or Ethylate). The precise mixtures depend upon the oil and its FFA Acid Number.

The plant of the present invention is capable of handling a range of oils, as it has both esterification and transesterification processes integrated into the design. The plant of the present invention is also preferably a continuous process.

BRIEF DESCRIPTION OF THE DRAWINGS

Various embodiments of the invention will be described with reference to the following drawings, in which:

FIG. 3A is plan view of the plant illustrated in FIG. 1.

FIG. 31 is an isometric view from a first side of a settling tank according to a preferred embodiment.

FIG. 32 is an isometric view from a second side of the settling tank illustrated in FIG. 31.

FIG. 32B is a side view of the settling tank illustrated in FIG. 31.

DETAILED DESCRIPTION OF THE PREFERRED EMBODIMENT

According to a particularly preferred embodiment, a portable biodiesel manufacturing plant is provided.

According to a preferred embodiment, the biodiesel manufacturing or processing plant for processing on continuous basis a process fluid from a raw plant based oil feedstock includes a housing containing main frame relative to which a power generation means and process equipment is mounted.

Figure 33:
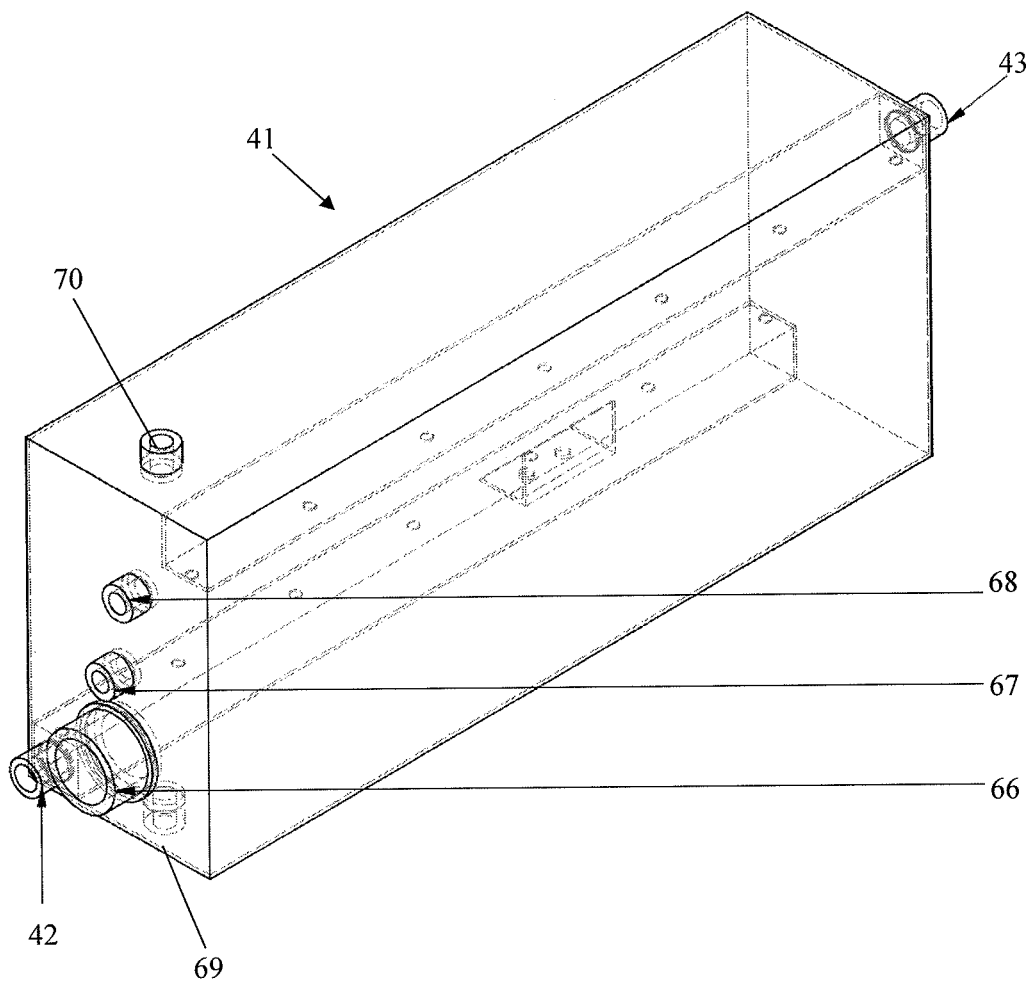
FIG. 33 is an isometric view of a heater tank according to a preferred embodiment of the present invention.

The process equipment includes an inlet for raw vegetable oil from an oil bearing plant crop or from waste vegetable oil from another source, a raw oil heating vessel 60 one preferred form of which is illustrated in FIG. 33, a trans-esterification subprocess including an alkali dosing mechanism to dose the process fluid in the presence of an alcohol, a powered sheer mixer to mix the alkali, alcohol and process fluid, a preferred form of which is illustrated in FIGS. 13 to 30, a reactor and primary separator 61 for separation according to gravity, a secondary separation for separation of alcohol from the process fluid through a differential pressure vaporisation process, and one or more settling tanks 62.

The plant of the present invention includes a trans-esterification subprocess including an alkali dosing mechanism to dose the process fluid in the presence of an alcohol and a reactor tank for primary separation of glycerol from the process fluid. Suitable process equipment is provided in the plant to facilitate this sub-process.

The process fluid is subjected to a trans-esterification sub-process in order to form the preferred fatty acid methyl ester (FAME). The trans-esterification sub-process will normally be after primary esterification or if the raw vegetable oil does not require esterification as a pre-treatment, after primary heating.

The process fluid once mixed with appropriate chemicals for trans-esterification will normally proceed to a trans-esterification settling tank, or a reactor tank. The residence time in the reactor tank will be dependent upon required production output, temperature, and the size of the reactor tank will typically be determined according to the maximum production output and required residence time. It may also be dependent upon the particular raw oil feedstock.

The alcohol used will preferably be methanol or ethanol or another alcohol could be used in the trans-esterification sub process.

Again, the mixing or dosing of the process fluid with the alkali in the presence of an alcohol takes place in a mixing vessel in order to ensure a consistent mix with two pumps provided in order to dose the alkali and/or the alcohol into the process fluid.

The preferred alkali is sodium or potassium hydroxide and methanol or ethanol as the reagent. A preferred mixture is known sodium (or potassium) methylate (or ethylate).

Figure 1:
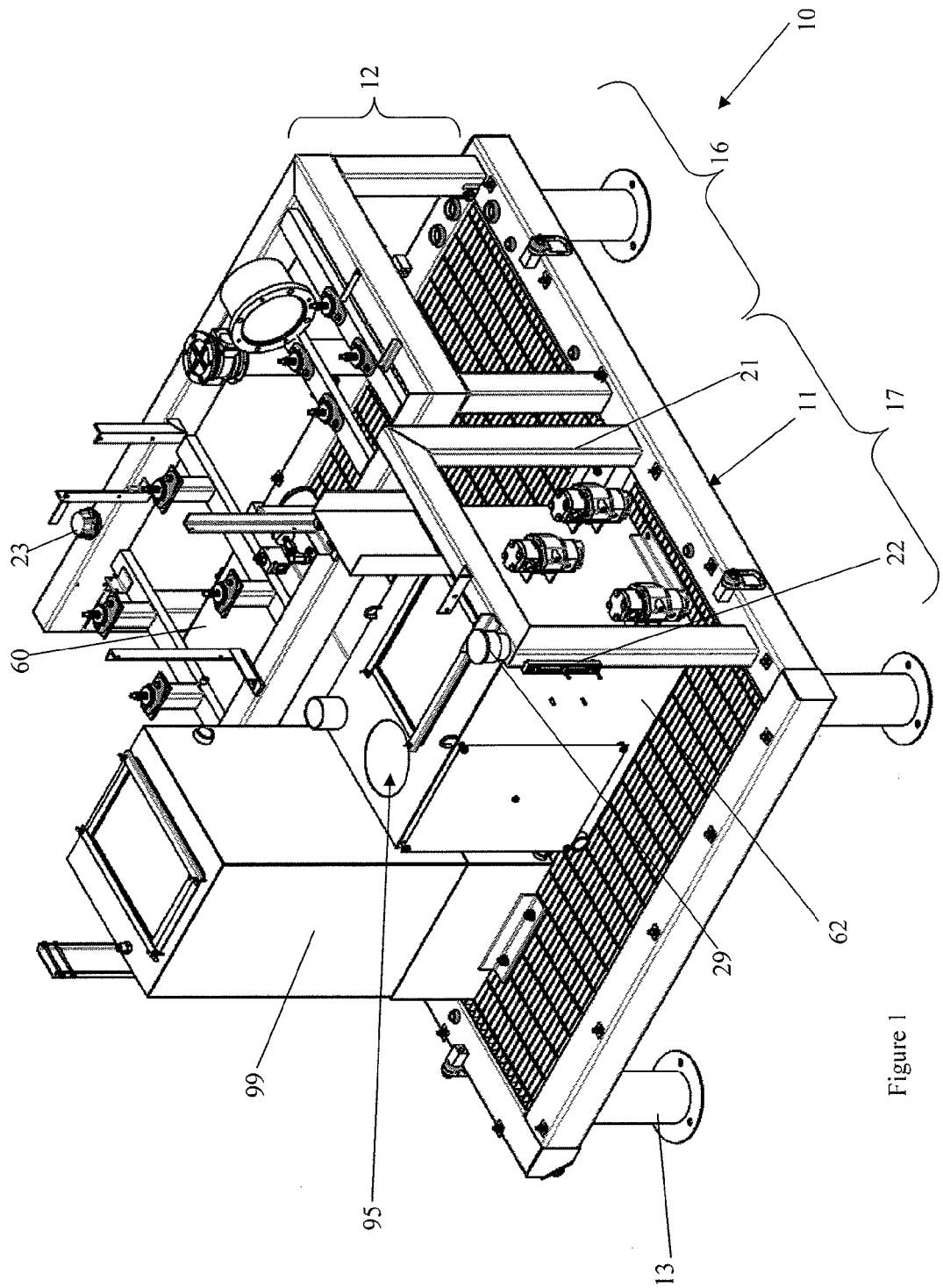
FIG. 1 is an isometric view from a first side of the plant of a preferred embodiment of the present invention.

The housing 50 for the plant of the illustrated preferred embodiment is preferably a container mountable relative to an internal frame assembly a preferred form of which is illustrated in FIG. 1. Typically, the frame assembly 10 includes a base or main frame 11 to which is mounted an engine mounting frame subassembly 12.

The main frame assembly 11 is usually mounted 450 mm above the ground but adjusters in the anchor legs 13 may be provided to permit the unit to be leveled.

Figure 4:
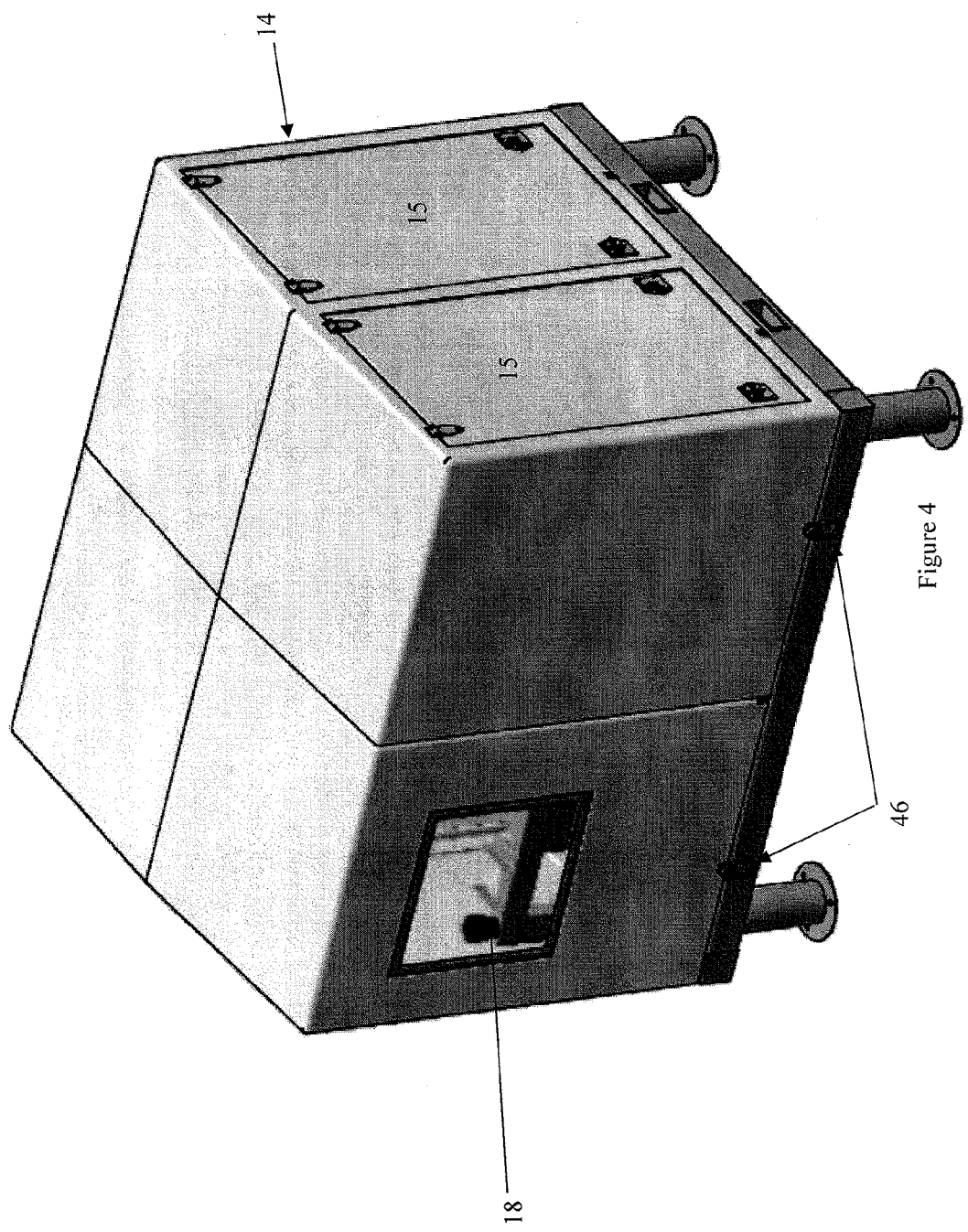
FIG. 4 is an isometric view of the container or housing of a particularly preferred configuration of the present invention.

The housing 14 (a preferred form of which is illustrated in FIG. 4) is normally provided as a lightweight, typically plastic housing with a number of doors 15 in order to allow access to the interior of the housing and ventilation through the housing, when the plant is operational.

Figure 2:
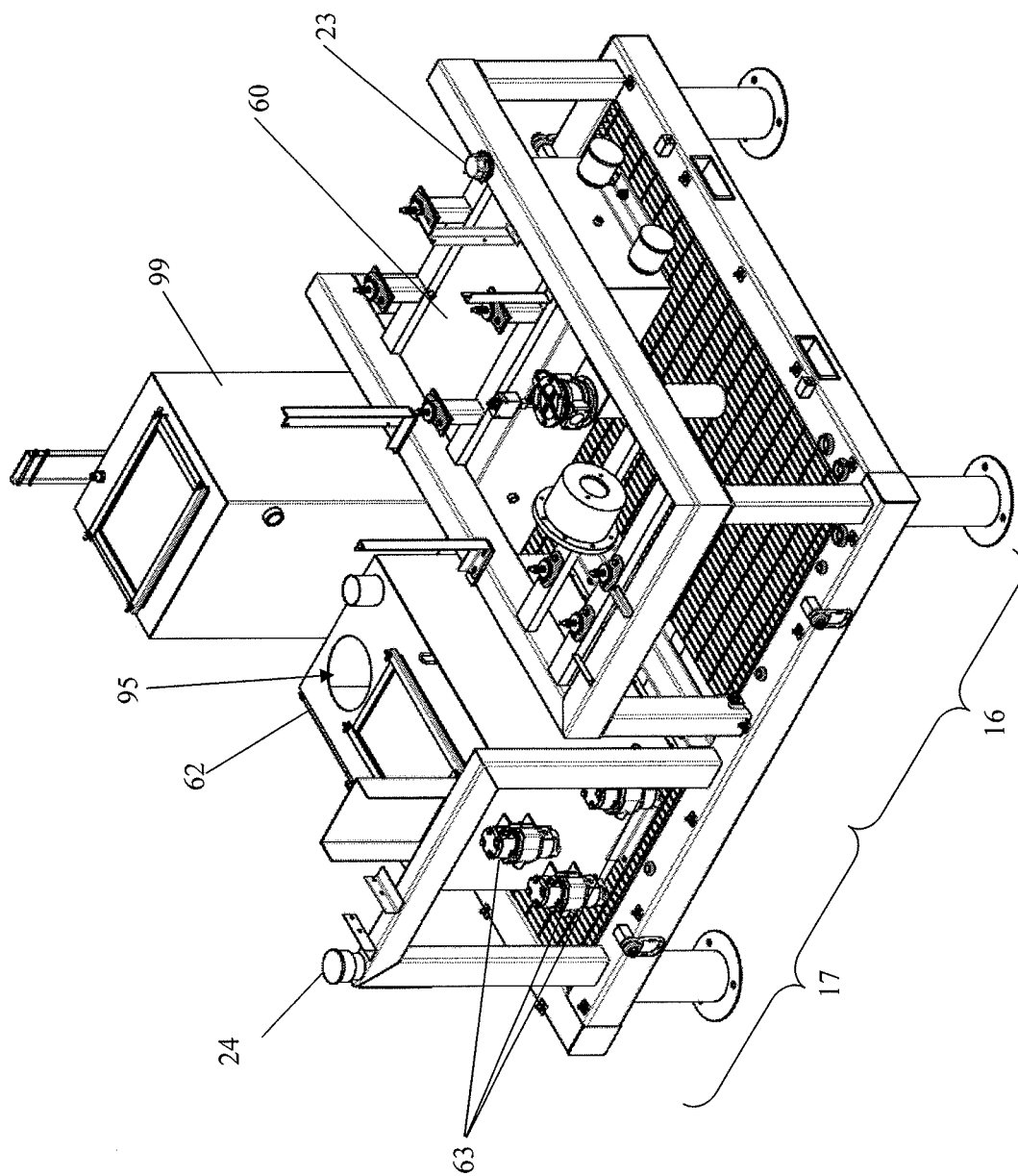
FIG. 2 is an isometric view from a second side of the plant illustrated in FIG. 1.
Figure 3B:
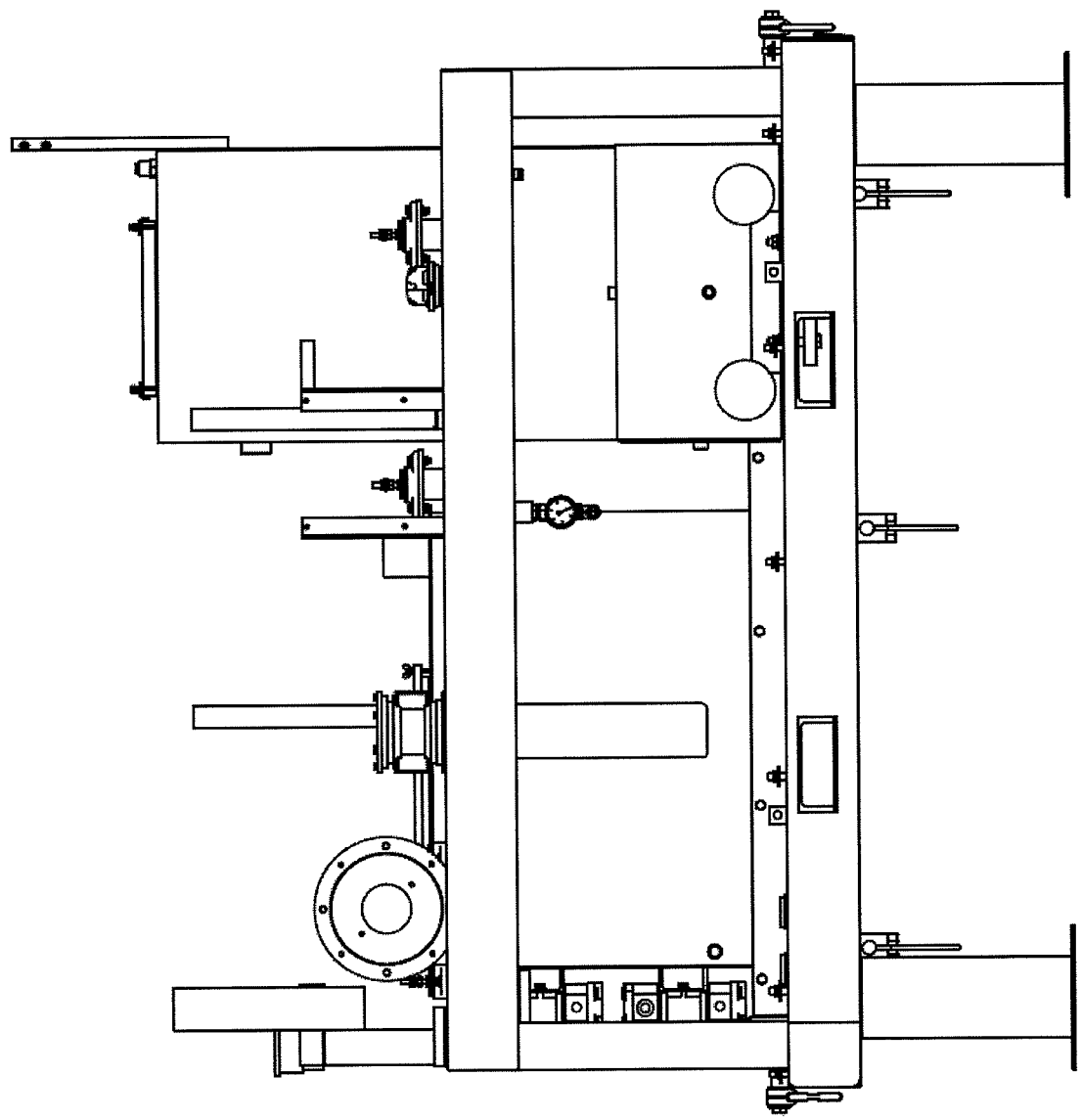
FIG. 3B is a side elevation view of the plant illustrated in FIG. 3A from the direction illustrated in FIG. 3A.
Figure 3C:
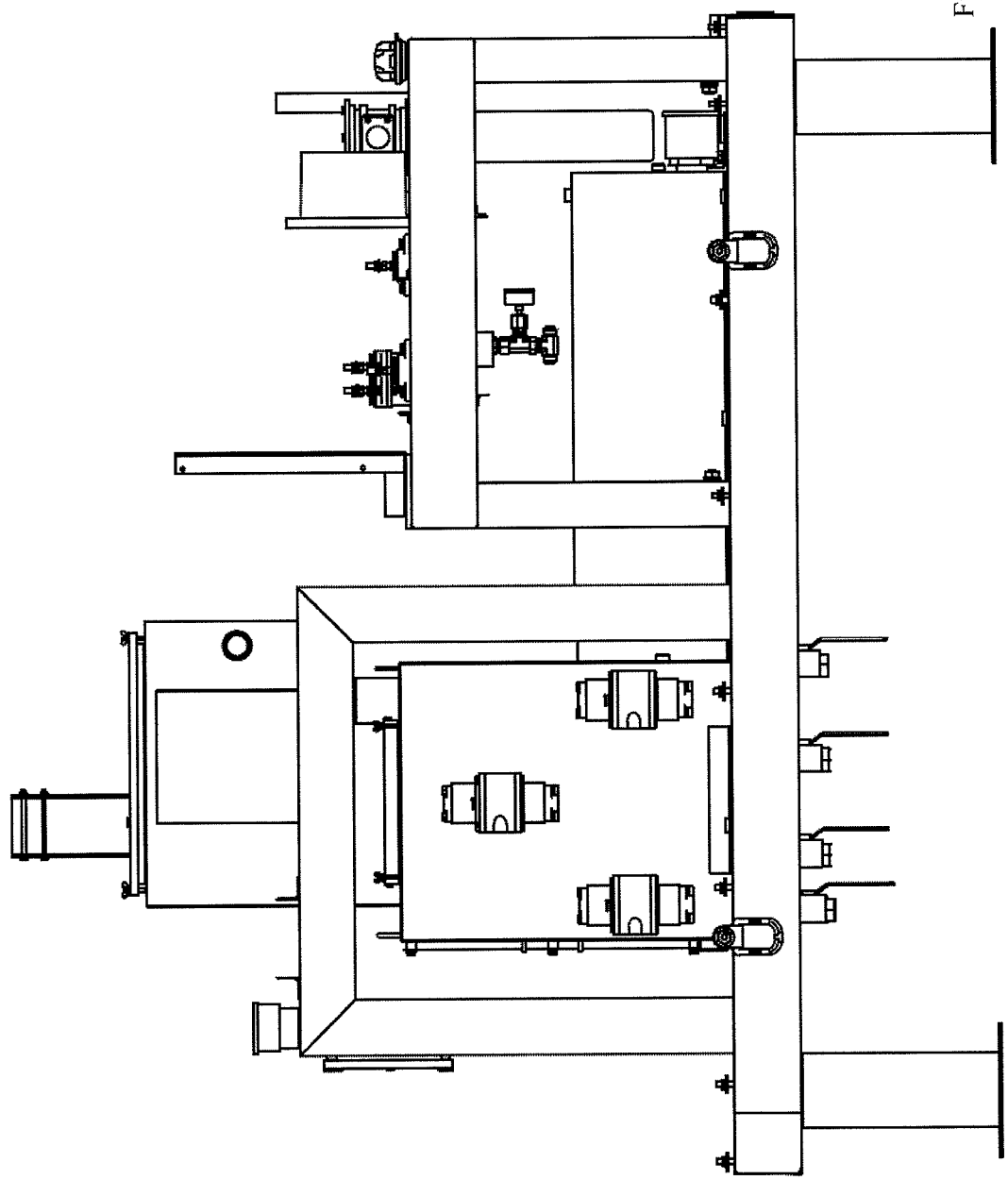
FIG. 3C is a side elevation view of the plant illustrated in FIG. 3A from the direction illustrated in FIG. 3A.
Figure 3D:
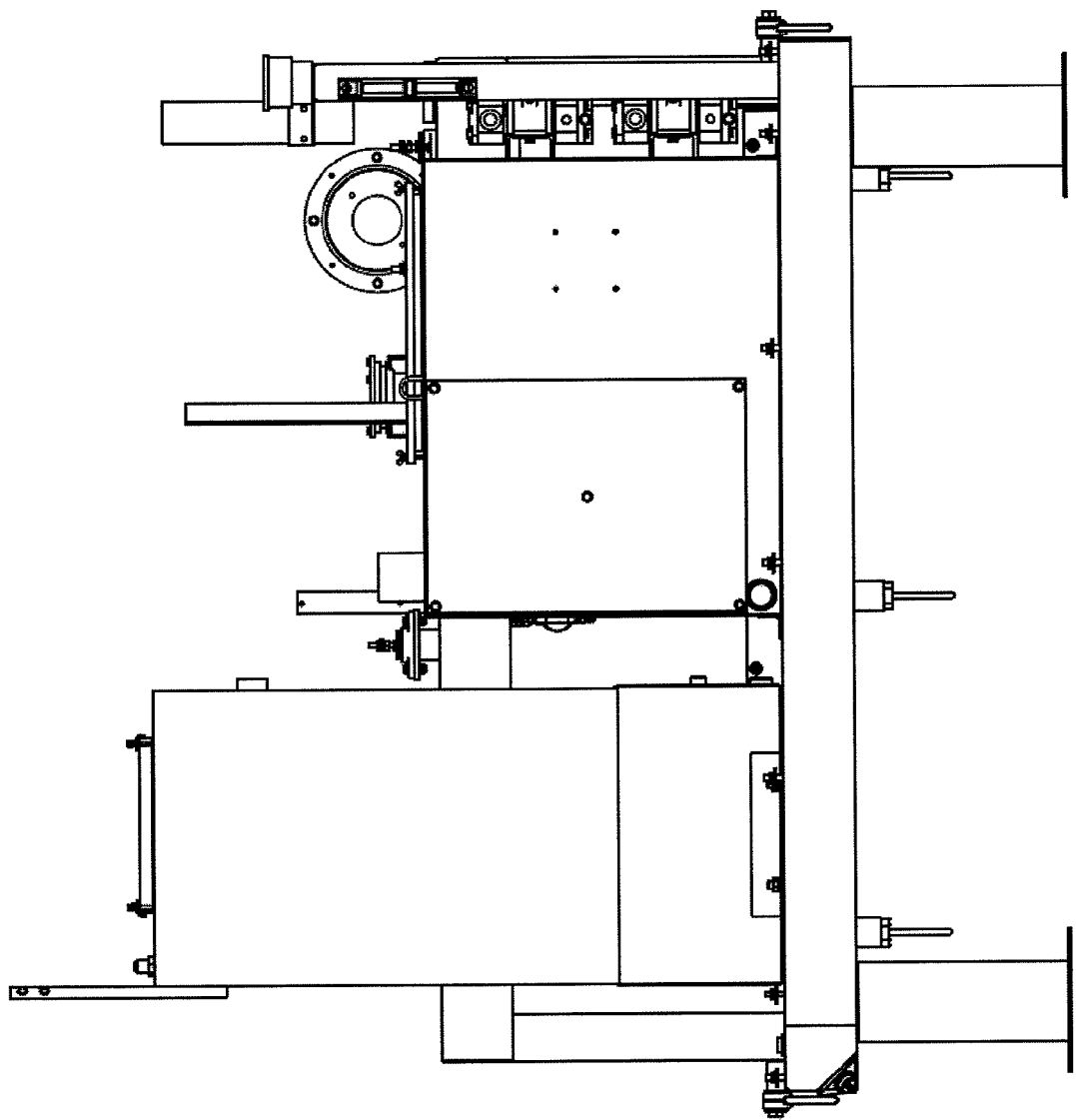
FIG. 3D is a side elevation view of the plant illustrated in FIG. 3A from the direction illustrated in FIG. 3A.

The interior of the housing will normally be divided into at least a pair of compartments in order to house particular components of the manufacturing plant. In particular, the orientation of the housing in FIG. 4 is the same as the internal configuration illustrated in FIG. 2. In particular, a first compartment 16 at one end of the housing 14 preferably contains the power generation means (not illustrated for clarity purposes) mounted on the engine mounting frame subassembly 12 and a second compartment 17 at the other end of the housing for the process equipment.

The housing 14 is preferably fully sealable from the environment, but will normally be provided with at ventilation openings and/or doors 15. It is preferred that ventilation driven by natural air flows is used. In order to provide such ventilation, doors 15 are provided in two of the sidewalls in order to allow the escape of heavier than air gases. One or more observation windows 18 may also be provided.

The housing is spaced above the ground surface or mount surface to promote natural flow under the container and circulation within the process area within the housing through a mesh or grate floor provided in the main frame assembly 11.

The main frame assembly 11 will normally be provided with lifting/securing/transport points 46. Lift points 46 of the preferred embodiment are provided at at least some of the corners of the main frame assembly 11, normally at each of the four corners adjacent each corner such that at least two points are provided on each of at least two sides of the container.

Normally, the main frame assembly 11 is provided with a plurality of legs 13. A particularly preferred height will be 450 mm above the ground or mount surface. It is preferred that the legs 13 used to mount the container are adjustable to allow for height adjustment of the main frame assembly and also to provide levelling capabilities.

The container and/or the legs 13 of the main frame assembly will normally be mounted relative to a plinth or slab laid on the ground surface. The slab will preferably be or include concrete and will normally be reinforced.

Figure 5:
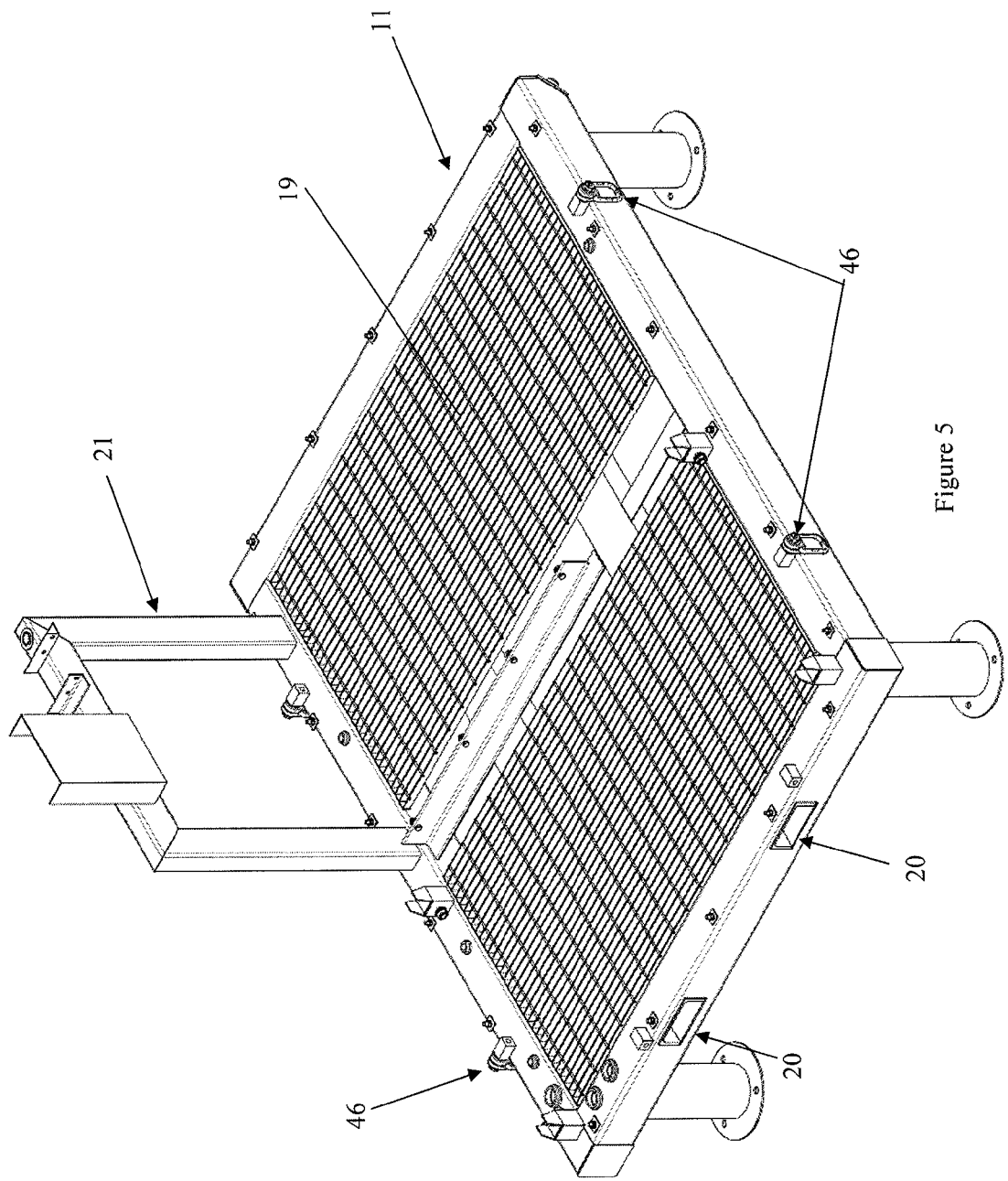
FIG. 5 is an isometric view of the main frame of a particularly preferred configuration of the present invention.

As illustrated in FIG. 5, the main frame assembly 11 includes a base wall platform 45 relative to which the components of the plant are mounted. Normally, the shape of the platform is defined by a rigid frame made of a plurality of frame members 47.

Each frame member 47 is rigid and strong and for this reason, a metal is preferred. Each frame member 47 will also preferably be substantially hollow. According to a preferred embodiment, the frame members 47 used will not only function to support the platform 45 to which the components of the plant are mounted, but can also typically be used to store fluids at least temporarily. The main frame assembly 11 is typically used to store hydraulic oil or similar for operation of the power generation means or process equipment and the engine mounting frame subassembly 12 will be used to store diesel fuel used to power the power generation means until production capacity allows the biofuel to be substituted. Therefore, the frame members 47 of each assembly will typically be linked to one another to form a storage tank.

The platform 45 will typically take the form of a substantially planar member attached to the frame. The platform 45 illustrated is a rigid mesh as this may increase airflow through the plant during operation.

Figure 6:
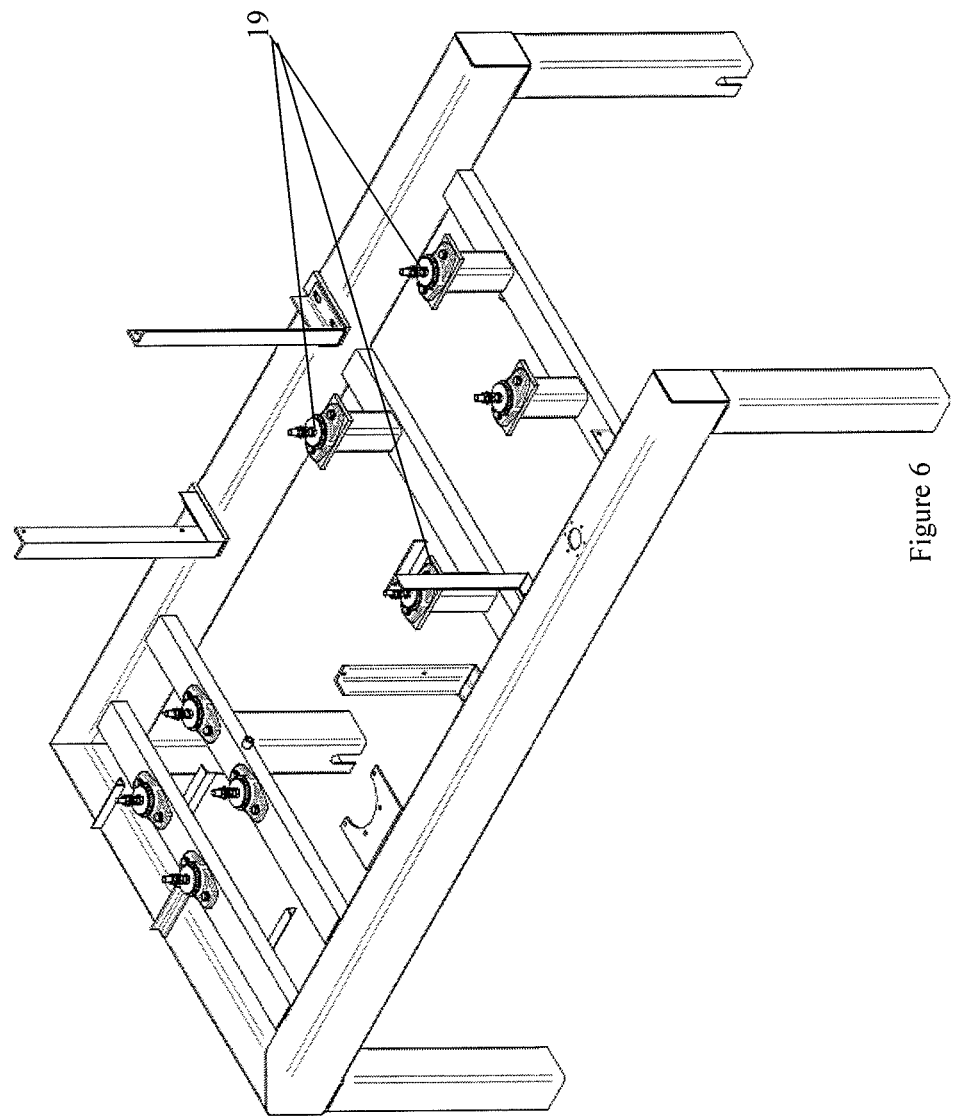
FIG. 6 is an isometric view of an engine frame assembly according to a particularly preferred embodiment of the present invention.

As mentioned briefly above, an engine mounting frame subassembly 12 is typically mounted to the main frame assembly 11 in order to mount a power generation means relative to the main frame assembly 11, but separately to the process equipment. A preferred form of the engine mounting frame subassembly is illustrated separately in FIG. 6 allowing the mounting of the power generation means partially above the process equipment on the main frame assembly 11 illustrated in FIG. 5.

Anti vibration mounts 19 are typically provided between the engine mounting frame subassembly and power generation means.

Also illustrated in FIG. 5 are the forklift tyne openings 20 in the main frame assembly 11 which allows the plant to be moved using a conventional forklift. A mounting assembly 21 for the control equipment is provided on the main frame assembly 11 and a fluid level gauge 22 is also provided an upright of the mounting assembly 21.

The engine mounting frame subassembly is also preferably provided in a fluid tight configuration and preferably functions as a tank for diesel fuel (either fossil or biodiesel) which can be used to power the power generation equipment. Normally, there will be a gauge or similar level indicator associated with each of the engine mounting frame subassembly and the main frame assembly. A fill point 23 is illustrated in FIGS. 1 to 3D for replenishing the diesel fuel in the engine mounting frame subassembly 12 and a fill point 24 is also illustrated in those Figures for replenishing the hydraulic oil in the main frame assembly 11.

The housing is provided with walls in order to enclose the plant. It is preferred that a number of doors 15 or other openings are provided in the walls of the housing.

During operation, the doors 15 are opened, again to promote airflow through the plant but the doors 15 will normally be closed or sealed for transport and prior to location onsite. The doors 15 can also be closed when the plant is not in operation in order to secure the plant against local wildlife or potentially against vandals. According to the preferred embodiment, a pair of doors 15 are provided in each of the end walls (the end walls being located adjacent either the power generation means or the process equipment).

An access panel 49 with observation window 18 is provided to access the controls (not shown) for the plant which are mounted on the mounting assembly 21.

The walls and doors or movable members will typically be formed from a light metal but materials such as plastic, provided it is sufficiently rigid and strong could be used in the alternative.

According to a preferred embodiment, the mixer 110 is provided having a number of mixing bodies 111, the axis of rotation for each of the mixing bodies offset by 120°.

According to the preferred embodiment illustrated in FIGS. 13 to 25, a cylindrical mixer is provided. An alternative configuration of mixer is provided in FIGS. 26 to 30 in which substantially rectangular intermediate body portions are used.

The mixer 110 of both of these preferred embodiments includes an outer housing having a central longitudinal axis, a top end portion 112, a bottom end portion 113 and a pair of intermediate portions 114.

Each portion has at least three toothed mixing bodies 111 associated therewith. The toothed mixing bodies 111 of the respective portions interengage and each rotates about a central axis, with the respective axes offset radially and spaced along the central longitudinal axis of the mixer 110.

The housing is typically modular in nature with a number of portions being attached together to form the mixer, with the number of portions and their particular configuration chosen according to the application.

As illustrated, the body portions mount the mixing bodies. According to the illustrated embodiments, the body portions are basically solid portions with a number of openings (obscured) therein to at least partially receive the mixing bodies.

According to the first preferred embodiment illustrated in FIGS. 13 to 25, each of the body portions whether intermediate 114 or end portions have a circumferential, transversely extending flange 115 with a number of openings 116 there through in order to receive elongate fasteners (not shown) to attach the portions to each other. Each intermediate portion will typically have a pair of transversely extending flanges, one at either end, and each end portion will typically have a single transversely extending flange.

In an alternative embodiment, each of the body portions, whether intermediate or end portions may have a solid circumferential portion such as that illustrated in FIGS. 26 to 30, having a number of openings 116 there through in order to receive elongate fasteners (not shown) to attach the portions to each other.

The illustrated body portions are fixed together using elongate fasteners extending substantially parallel to the longitudinal axis of the housing. Normally, these elongate fasteners are threaded rods and using the rods, a compressive force can be applied to the end portions and the sandwiched body portions, to seal the respective end and intermediate body portions together.

The body portions illustrated are stepped portions. Normally, the number of steps in each body portions equals the number of mixing bodies 111 which the body portion mounts.

Figure 29:
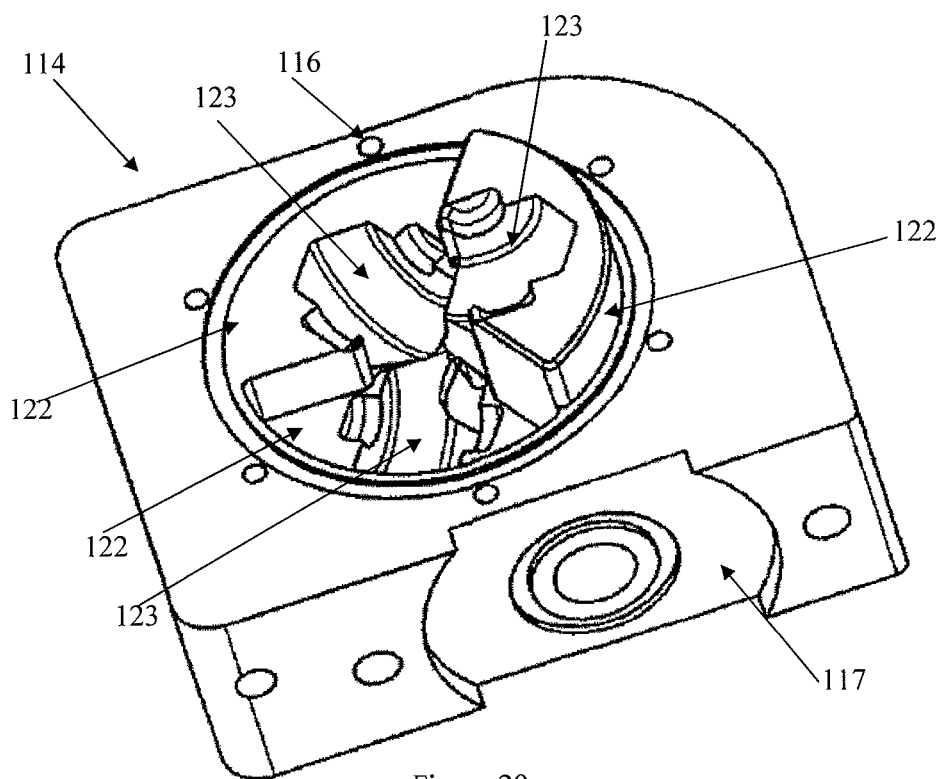
FIG. 29 is an isometric view of an upper intermediate portion of the mixer according to a preferred embodiment, with the mixing bodies removed.
Figure 30:
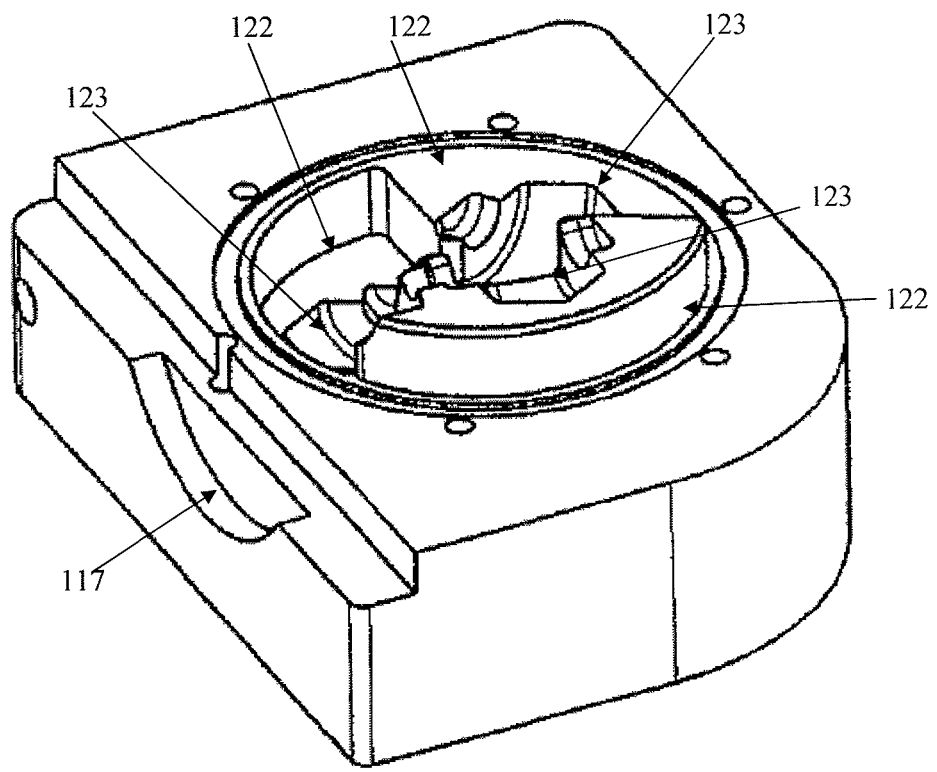
FIG. 30 is an isometric view of a lower intermediate portion of the mixer according to a preferred embodiment, with the mixing bodies removed.

As best illustrated in FIGS. 29 and 30, a drive means (not shown) will normally be provided to attach to one or more intermediate portions 114 via an attachment depression 117 and the drive means will normally extend into the housing. Because the mixing bodies in the mixer interengage with one another, driving one of the mixing bodies 111 causes sympathetic rotation of the other mixing bodies. One example of drive means which may be used is a driveshaft associated with a bevelled or mitred gear to mesh with at least one of the mixing bodies.

According to the embodiment illustrated in FIGS. 29 and 30, a driveshaft (not shown) extends into the housing substantially perpendicularly to the main longitudinal axis of the housing, through two of the intermediate portions 114.

Figure 26:
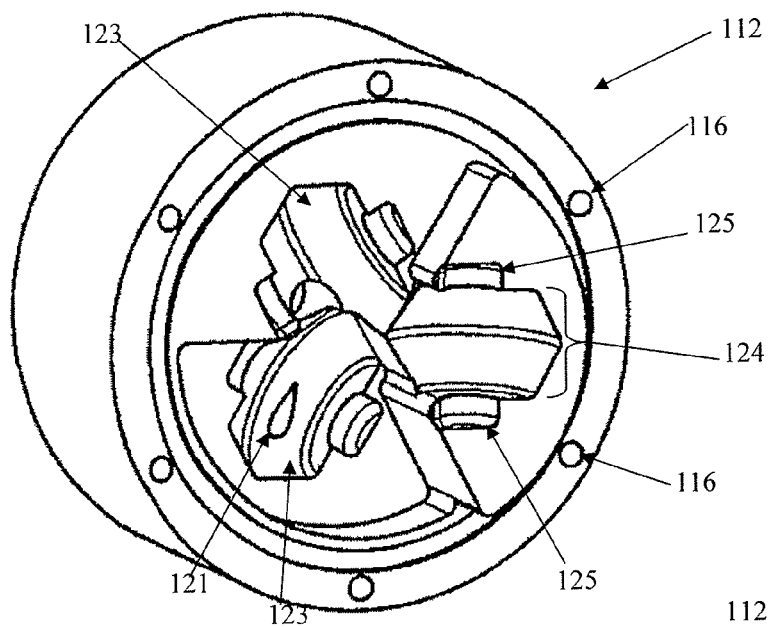
FIG. 26 is a view from above of the top portion of a mixer according to a preferred embodiment of the present invention, with the mixing bodies removed.
Figure 27:
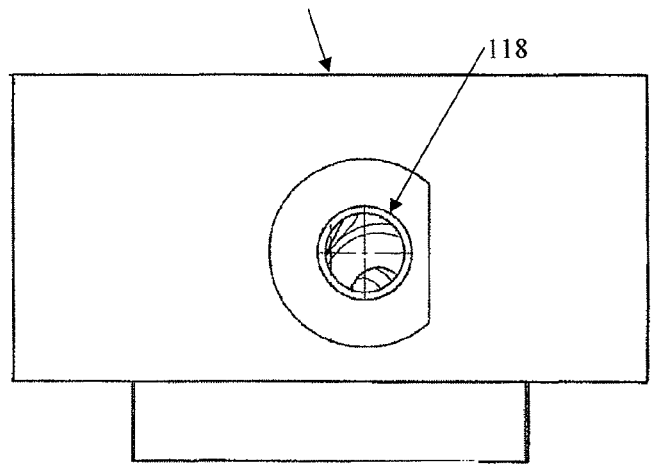
FIG. 27 is a side view of the top portion of a mixer illustrated in FIG. 26.
Figure 28:
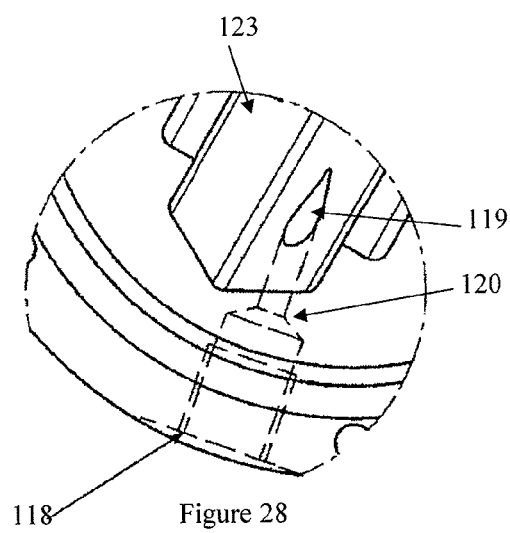
FIG. 28 is a detailed view of the inlet of a mixer according to a preferred embodiment.

The top end portion of the preferred embodiment illustrated in FIGS. 26 to 28 has an inlet 118. The inlet 118 provided allows injection of material directly onto at least one of the mixing bodies 111. The preferred form of inlet includes a conduit 120 which extends perpendicularly to the central longitudinal axis of the housing through the body of the end portion.

The inner end 119 of the inlet is shaped in order to correspond with the external shape of a mixing body and the inner end is provided in a shaped opening located in a sidewall of an opening that receives a mixing body. In this way, the end of the inlet illustrated closely matches the shape of the mixing body 111 to spread the material introduced into the mixer over a shaped area 121 of the mixing body 111.

The bottom portion has an outlet. The material will then move through the mixer 110 using the force of gravity as well as being forced through the mixer by the rotation of the mixing bodies 111.

Each of the end portions illustrated is configured to receive and locate three mixing bodies 111. Each end portion has an outer side and an inner side. The inner side of the end portion has a stepped configuration to receive multiple mixing bodies 111, with the number of steps 121 equaling the number of mixing bodies 111.

According to the illustrated preferred embodiment, where the end bodies mount three mixing bodies 111, the end body portion has three steps 122 at different levels on the inner wall. In this embodiment, each end of each body portion is divided into three steps 122, with each step being approximately 120° of arc.

According to the illustrated configuration, each end portion has three steps 122, each configured as a 120° arc portion, one of the 120° steps being a depression, and one being a 120° upstand. Further, each of the intermediate portions has three steps 122 at either end, each step configured as a 120° arc portion, one of the 120° steps being a depression, and one being a 120° upstand.

As illustrated in the preferred embodiment in FIGS. 29 and 30, there will be a shaped opening 123 in each step 122 to at least partially receive and positively locate each mixing body 111. Normally, each opening 123 in each step 122 receive half of height of the mixing body 111.

Each mixing body receiving opening illustrated in FIGS. 26, 29 and 30 has a main opening 124 and a pair of side openings 125 with the side openings 125 receiving laterally extending axles 126 provided on either side of the mixing body 111 and about which the mixing body 111 rotates. The main opening 124 receives a toothed portion 127 of the mixing body 111.

According to this described embodiment, the main openings 124 in the end portions will be depressions whereas the main openings 124 in any intermediate portions together define a circuitous path through which material can move under force provided by the mixing bodies 111 through the mixer from inlet to outlet whilst the side openings 125 will support the mixing bodies 111 for rotation.

The main openings 124 are closely shaped to correspond to the shape of the mixing bodies 111 in order to allow rotation of the mixing bodies 111 within the openings but to limit all other movement. The toothed portion 127 of the mixing body 111 has a tight tolerance with the walls defining the main opening in the end portions.

According to the illustrated mixer, three mixing bodies are mounted between the end surface of an intermediate portion and the inner wall of the adjacent end portion. Further, three mixing bodies are mounted between adjacent end surfaces of adjacent intermediate portions.

Again, according to the particularly preferred embodiment, typically three mixing bodies are "sandwiched" between the end walls of adjacent body portions. Therefore, each intermediate portion will typically mount six mixing bodies or two pairs of three mixing bodies (one pair of three located at each end wall) according to the illustrated preferred embodiment.

Each of the preferred mixing bodies 111 illustrated is substantially circular in configuration. As mentioned above, each of the mixing bodies 111 has a pair of axles 126, one extending from each side of a central toothed portion 127.

Each of the mixing bodies 111 illustrated is shaped as a double mitre gear.

When viewed from the side, each mixing body 111 has an axle 126 extending from either lateral side of a substantially hexagonal shaped central toothed portion 127. The axles 126 extend from a substantially circular sidewall which may be concave. The other walls of the hexagonal shaped central toothed portion are typically frustoconical in shape (with the large diameter portions back to back) and are provided with a plurality of teeth.

The angle of the mitre will differ according to the number of mixing bodies included in the mixer. However, according to the illustrated preferred 120° offset configuration, each of the mitre gear shaped mixing bodies 111 has a pair of toothed surfaces extending circumferentially around the mitre gear shaped mixing body 11, each of the toothed surfaces extending at an angle of approximately 30° to the axis of rotation of the mixing body 111.

The teeth may have any shape and/or configuration. For example, the teeth illustrated have a straight configuration. The mixing bodies of the preferred embodiment will typically have a low ratio in order to convert the majority of the force into mixing force. Further, the teeth may have any shape such as straight, or coniflex for example, with the shape of the teeth chosen to maximise the particular form of mixing which is desired.

Typically, the central axes of respective mixing bodies 111 are spaced along the length of the central longitudinal axis of the housing in a repeating pattern.

The central axes of adjacent mixing bodies of adjacent portions are radially offset from one another.

The mixer will typically have an associated speed regulation system in order to control the speed of the mixing bodies.

The reactor tank 61 is located after the alkali mixing process in order to allow time for the transesterification reaction to occur and to achieve primary separation of the glycerol from the FAME, primarily by settling. The reactor tank 61 of the preferred embodiment can be a substantially rectangular process vessel with a tapered lower portion to allow the heavier fluid to be drawn off from a lower portion of the reactor tank. The reactor tank 61 is situated such that it uses the adjacent raw oil tank 60 as a heat exchanger. There will normally be an inlet in the upper portion for the process fluid to be separated. At least one, and preferably multiple outlets are provided spaced across the width of the lower portion of the reactor tank. The internal volume of the reactor tank may be provided with one or more internal baffles or separating parts over which the clear FAME flows leaving the heavier components behind to be drawn off.

The reactor tank therefore preferably functions as both a reactor tank and a settling tank. Removal of one or more of the products from the reactor/settling tank, typically the glycerol, can be used to drive the transesterification reaction to higher conversions.

Figure 32A:
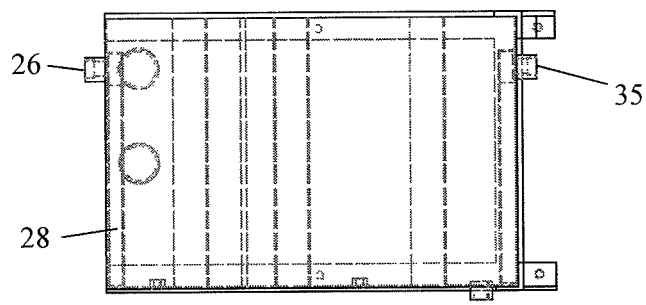
FIG. 32A is a plan view of the settling tank illustrated in FIG. 31.
Figure 32C:
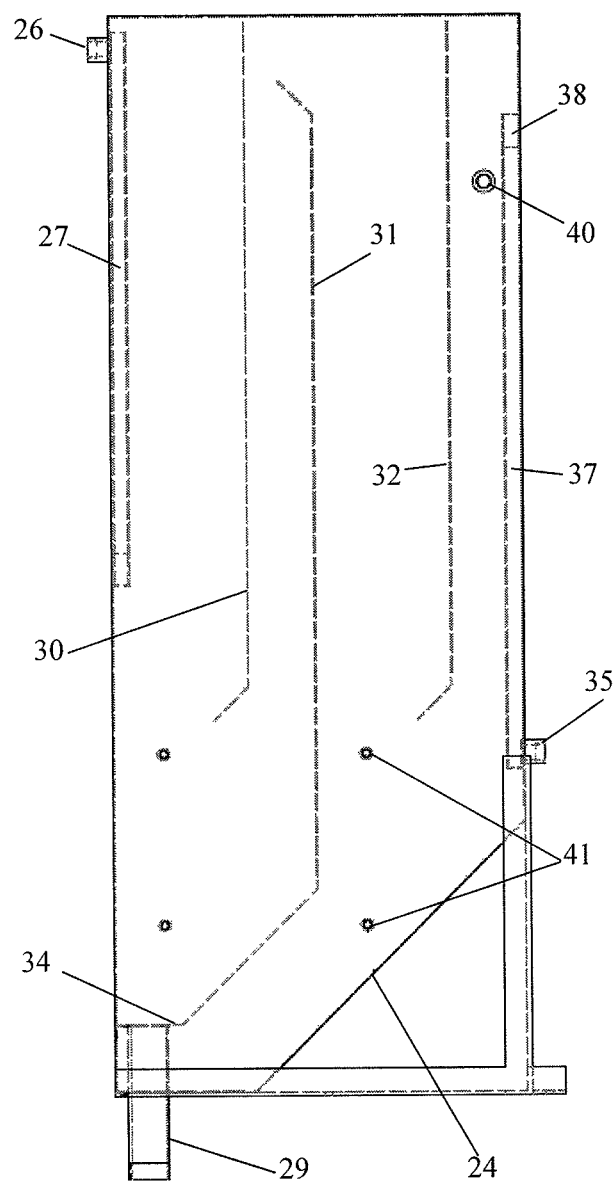
FIG. 32C is a front view of the settling tank illustrated in FIG. 31.
Figure 32C:
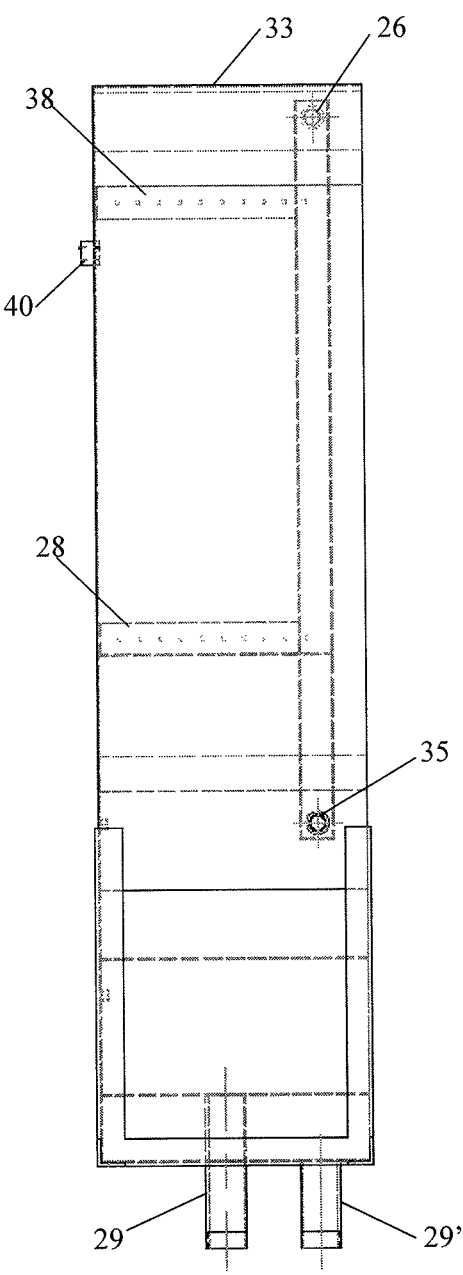

According to the alternative preferred embodiment illustrated in FIGS. 31 and 32, a combined reactor tank and settling tank 65 can be provided. The combined reactor tank and settling tank illustrated functions as a reactor tank due to the residence time of the fluid in the tank. Also due to the residence time and the particular configuration of the internal baffle assemblies within the tank, the tank will also function to separate lighter fluid fractions from heavier fluid fractions. The heavier and lighter fluid fractions can be drawn off separately.

In particular, the reactor tank and settling tank is generally rectangular but with a tapered wall 24 which tapers to a generally planar basewall 25. A pair of outlets 29 and 29' are located through the generally planar basewall 25 but the origin of each of the outlets differ.

An inlet 26 is provided at the upper portion of the reactor and settling tank, generally above the outlets. The inlet 26 is configured as a tubular inlet with a substantially vertical conduit portion 27 connected to at least one substantially horizontal arm 28 with a number of openings therein to allow fluid which enters the reactor and settling tank through the inlet 26 to be dispersed within the tank.

As mentioned previously, the tank has an internal baffle arrangement which assists with the settling. In particular, a substantially vertical first baffle 30 extends downwardly from an upper wall 33 is preferably provided spaced from the inlet 26. The lower portion of this first baffle 31 is typically directed downwardly and back towards the wall mounting the inlet 26. A second baffle 31 extends upwardly with a free end spaced from the upper wall 33 further from the inlet 26 than the first baffle 30. A lower portion 34 of the second baffle 31 abuts the wall mounting the inlet 26 and preferably, a first outlet 29 is provided in the lower portion. Normally, the heavier fraction of the fluid is drawn off from the volume between the second baffle 31 and the wall mounting the inlet 26. A third baffle 32 is typically provided spaced from the second baffle 31 further from the inlet 26 than the second baffle 31. The third baffle 32 preferably has a configuration similar to the first baffle 30.

A second outlet 29' is preferably provided in a lower portion of the reactor and settling tank 65 which allows fluid to be drawn off from the lowest point in the tank.

Still further, the third outlet 35 may be provided. As illustrated, the third outlet 25 is provided on the wall 36 opposite the wall mounting the inlet 26. This outlet 35 is preferably the opposite configuration to the inlet 26, being a tubular outlet with a substantially vertical conduit portion 37 connected to at least one substantially horizontal arm 38 with a number of openings therein to allow fluid entering the arm 38 to collect in the substantially vertical conduit portion 37 and proceed to the inlet 26. In the outlet configuration, the substantially vertical conduit 37 is normally below the horizontal arm 38 whereas in the tubular inlet configuration, the vertical conduit portion 27 is above the horizontal arm 28.

Fluid will typically flow through the reactor and settling tank in a circuitous route providing residence time and allowing the mixed fluid entering the reactor and settling tank to separate under gravity into different fractions so that the different fractions can be drawn off from different points within the reactor and settling tank 65

It is preferred that the outer vessel of the tank is fluid tight, normally of metal with a welded construction. The tank being generally rectangular normally has a lid or upper wall 33 which is typically fully welded to the remainder of the tank. Preferably, the tank is maintained in an upright position with the tapered wall 24 towards the lower end by a substantially L-shaped mounting foot 39 formed from a number of members. Other vents or inlet/outlets 40 can be provided through one or more sidewalls. Nuts 41 are welded in the wall to allow attachment to a portion of the frame assembly.

The vacuum evaporation separation assembly 301 used according to a preferred embodiment of the present invention operates on the principle that if a liquid is heated while under vacuum, the boiling point of the liquid will be decreased which will also reduce the amount of heat energy needed to boil the liquid. Therefore, by applying a vacuum and separating the more volatile alcohols from the less volatile FAME, a reduction in energy usage can be achieved and also typically more effective separation of the components.

Generally a heating step will be included but the heater may be located within the vacuum separation tower 303. Provided that the separated vapour can be removed and there is an outlet for the FAME, the configuration of the process vessel itself is not essential.

A heater of the preferred embodiment is preferably as illustrated in FIG. 33. The heater 41 can be used as a part of the vacuum evaporation process step but preferably, is used as a raw oil heater. The heater 41 is a generally rectangular vessel including an inlet 42 in a lower portion of one of the end walls and an outlet 43 in an upper portion of an opposite end wall. The inlet is configured as an elongate tubular inlet and the outlet is configured as an elongate tubular outlet, each with a number of openings in the sidewall of the tube for dispersion of the liquid within the heater 41.

A thermometer 68 is typically provided in the heater 41 in order to assess the temperature in the heater. A level switch is 67 typically used in order to ensure that sufficient fluid remains in the heater 41 for use in the process. Normally, a drain 69 is also provided through a lower wall of the heater and a vent 70 is provided through an upper wall.

The heater is normally heated through the provision of a heating element or similar which typically is located within the heater through a heater socket 66. The heater socket 66 is normally provided in one of the end walls.

Figure 9:
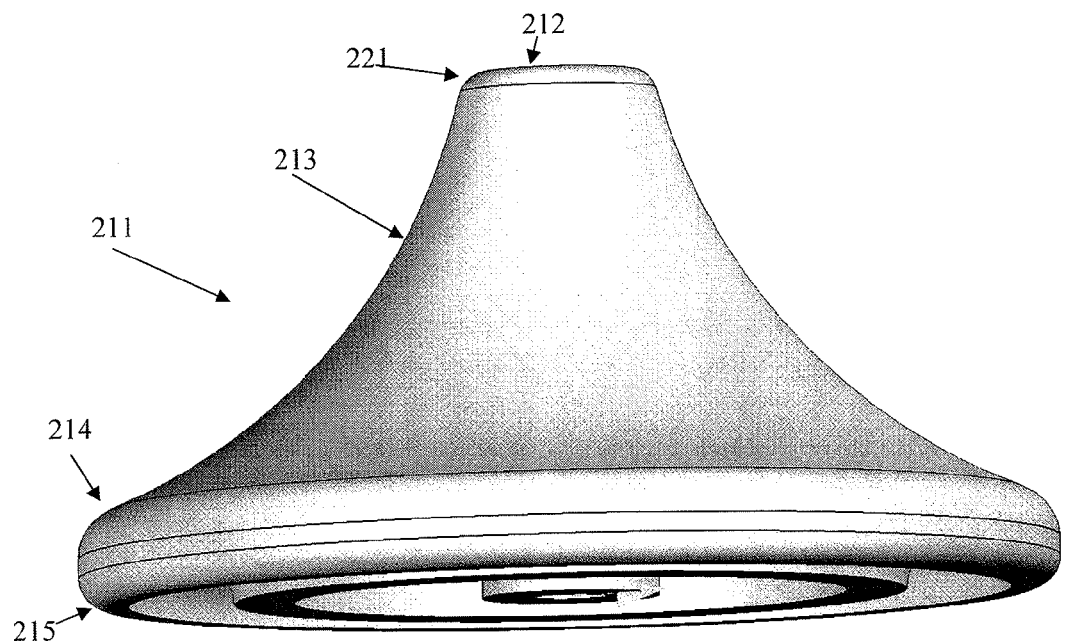
FIG. 9 is a side view of a separator support module according to a preferred embodiment of the present invention.
Figure 10:
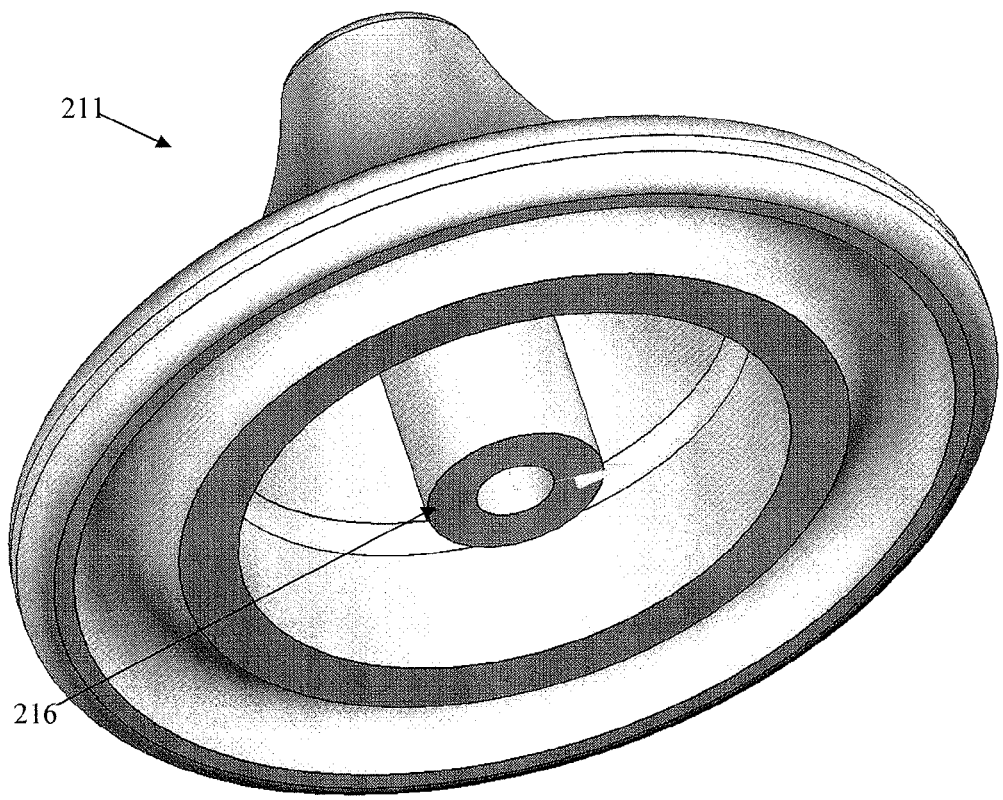
FIG. 10 is a view from beneath the separator support module illustrated in FIG. 9.
Figure 11:
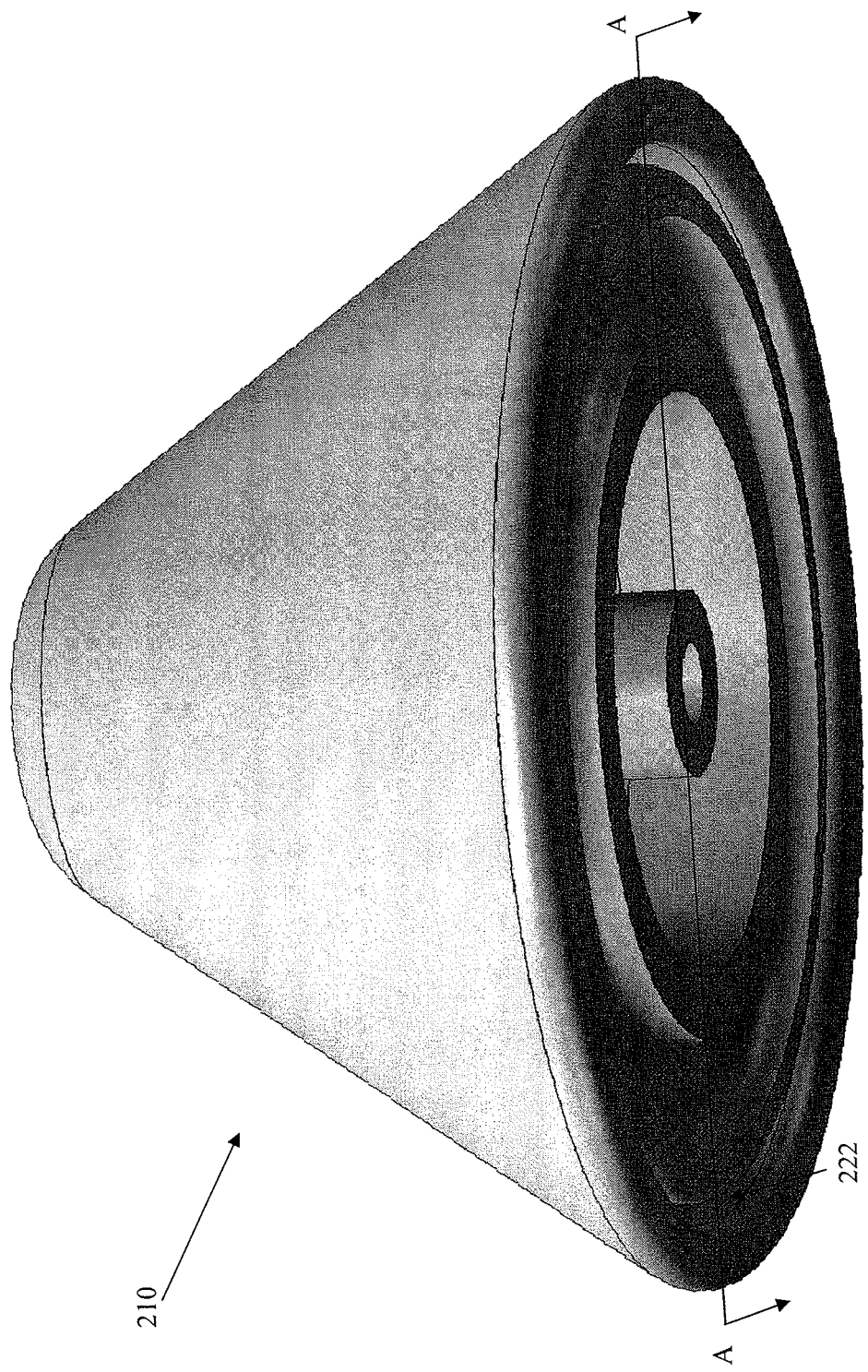
FIG. 11 is a view from beneath an assembled separator according to a preferred embodiment of the present invention.

According an alternative embodiment, a chantrelle separator 95 may be used instead of the vacuum evaporation separation assembly 301. Where provided, the chantrelle 95 is preferably located directly above and in fluid communication with the secondary settling tank 62 (indicated on FIGS. 1 and 2) and includes a substantially bell-shaped inner module 211 (illustrated in FIGS. 9 and 10) having a crown 212, waist 213, separation surface 214 and lip 215 with a mixture inlet 216 extending upwardly through the crown 212 and an outer hood 217 (illustrated in FIGS. 7 and 8) containing the inner module 211 and having a vapor outlet 218 opening therein, the inner module 211 mounted for rotation within the outer hood 217.

In operation, a heated fluid having at least one volatile component mixed therein, enters through the mixture inlet 216 and flows over the inner module 211 during rotation. Due to the shape of the inner module 211, the cross-sectional area of the separation surface 214 and lip 215 portions are approximately 100 times that of the mixture inlet 216 and the inlet flow is such that the thickness of the mixture on the inner module 211 reduces as it flows downwardly across the surface of the inner module 211.

A close fitting hood 217 is fitted, through which air is preferably drawn with a stimulated flow. Due to the shape of the inner module 211 and/or the hood 217, the airflow travels around the surface of the inner module 211 in a helical pattern. As the air rises through the air space between the inner module 211 and the hood 217, its velocity increases, and the pressure differential across the mass transfer or vapourisation surface of the liquid mixture increases, permitting the more volatile components of the mixture to escape the surface tension of the mixture and be carried off in the airflow, whilst the less volatile component(s) of the fluid flow down the inner module 211 and off the lip 215 to be collected below.

The degree of separation will be affected mainly by the relative volatilities of the components of the mixture as well as other parameters such as the temperature of the feed mixture, the inlet flow rate, the rotation speed of the inner module 211 and the flow rate of the air through the air space.

The separator 210 of the illustrated embodiment finds particular application in a biodiesel manufacturing process to separate methanol (more volatile component) from the fatty acid methyl ester (FAME) (less volatile component or mixture). The temperature of the FAME is preferably approximately 55° C. at the point of entry. The FAME passes through the separator 10 and is collected in a chamber (not shown) under the inner module 11.

Figure 7:
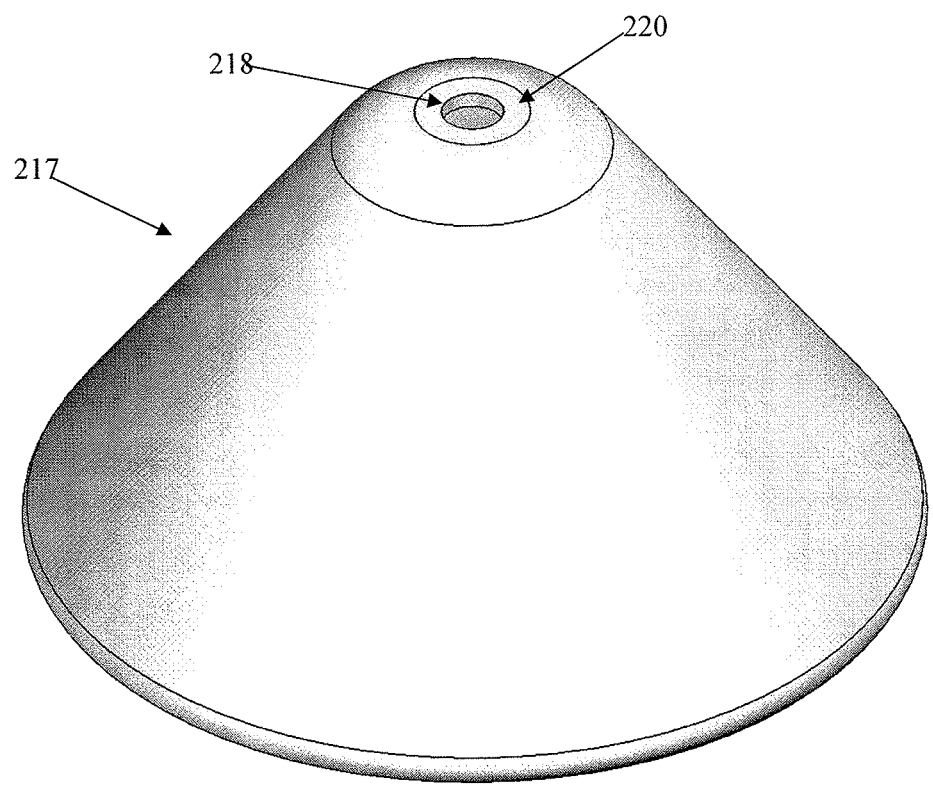
FIG. 7 is a view from above of a separator hood according to a preferred embodiment of the present invention.
Figure 8:
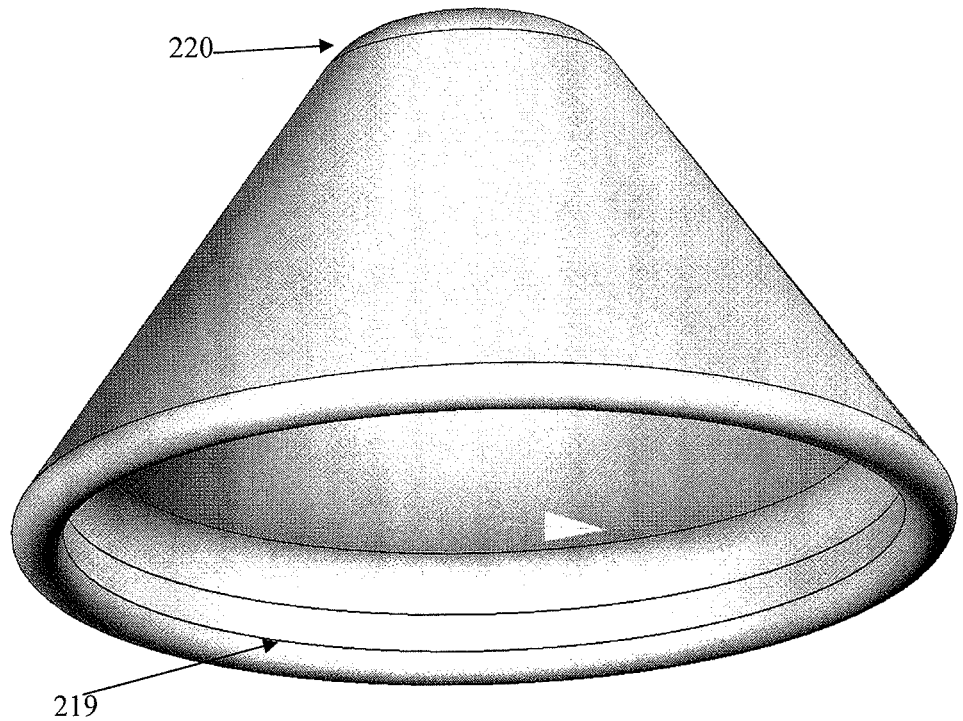
FIG. 8 is a view from below of the separator hood illustrated in FIG. 7.

As illustrated in FIGS. 7 and 8 in particular, the outer hood 217 is generally frustoconical in shape with an open bottom 219 and a crown 220. A single vapour outlet 18 is provided through the crown 220 of the outer hood 217.

The substantially bell-shaped inner module 211 is hollow and substantially circular in cross-section, although the dimension of the circular cross-section changes over the height of the module 211, narrowing towards the crown 12 of the inner module 211.

The mixture inlet 216 is substantially centrally located through the bell-shaped inner module 211, extending over the height of the inner module 211 from a plane adjacent or at the lip 215 of the inner module 211 and through the crown 212 of the inner module 211.

The crown 212 of the inner module 211 is arcuate, curving from the inlet 216 to an upper shoulder 221.

Figure 12:
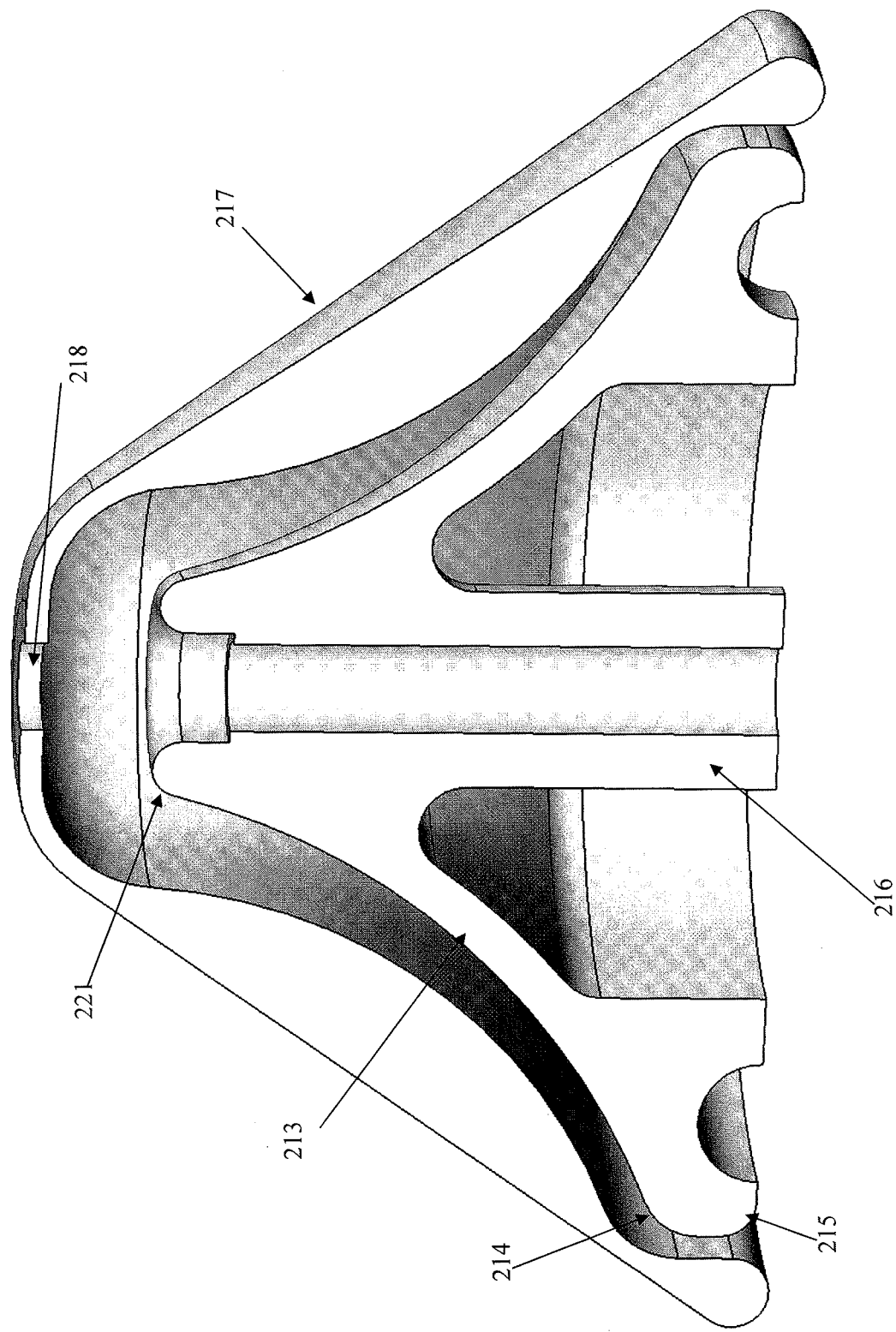
FIG. 12 is a sectional view of the separator illustrated in FIG. 11 along line A-A
Figure 13:
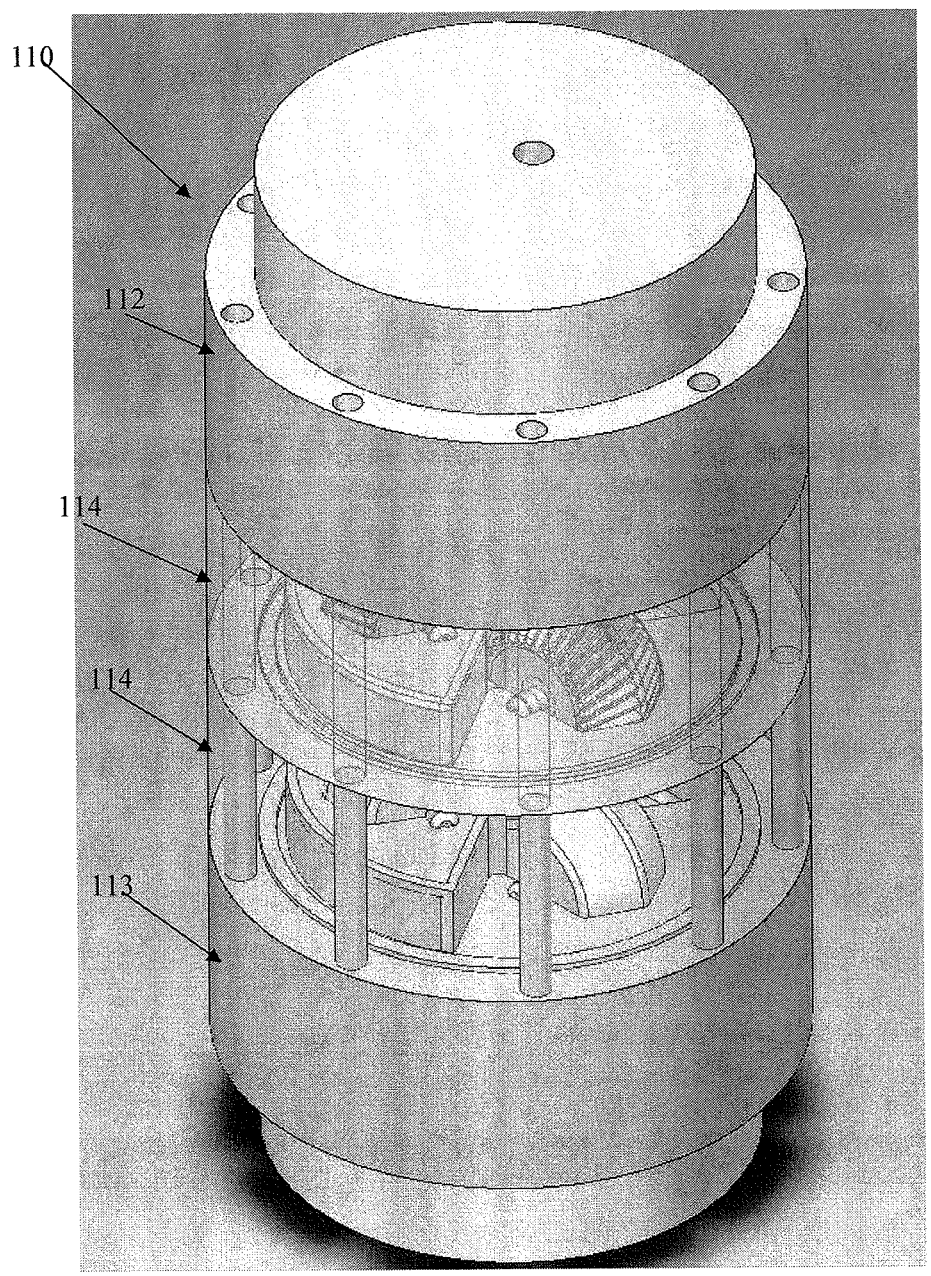
FIG. 13 is an isometric view of a mixer according to a preferred embodiment of the present invention.
Figure 14:
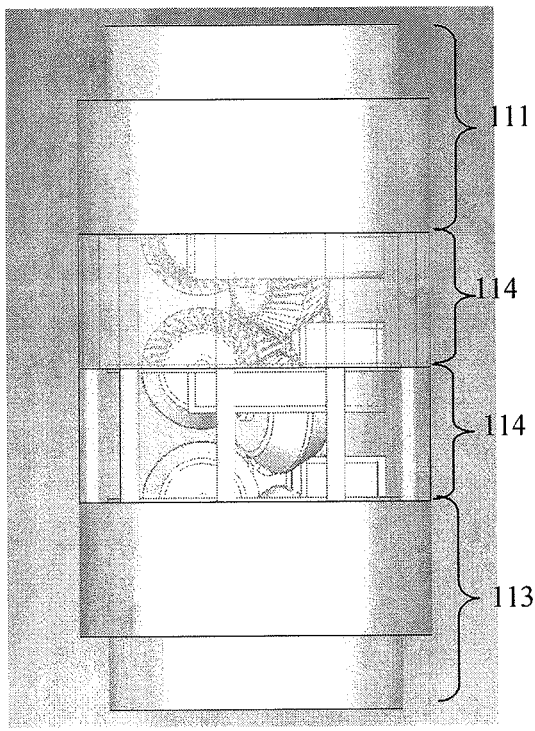
FIG. 14 is a view from the rear of the mixer illustrated in FIG. 13.
Figure 15:
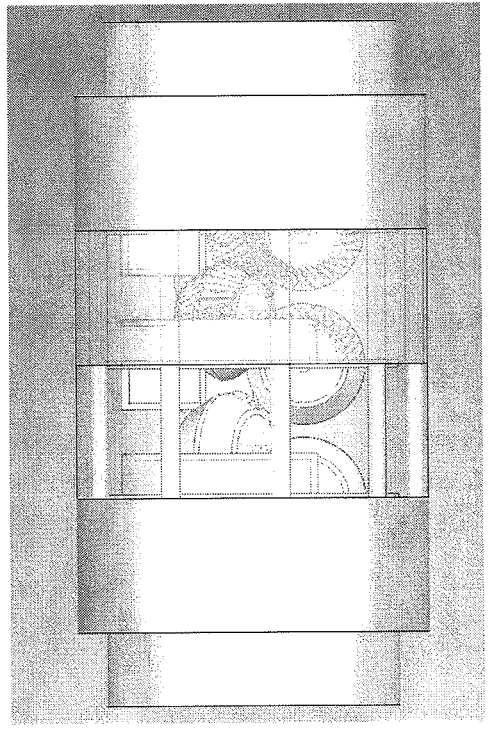
FIG. 15 is a view from the front of the mixer illustrated in FIG. 13.
Figure 16:
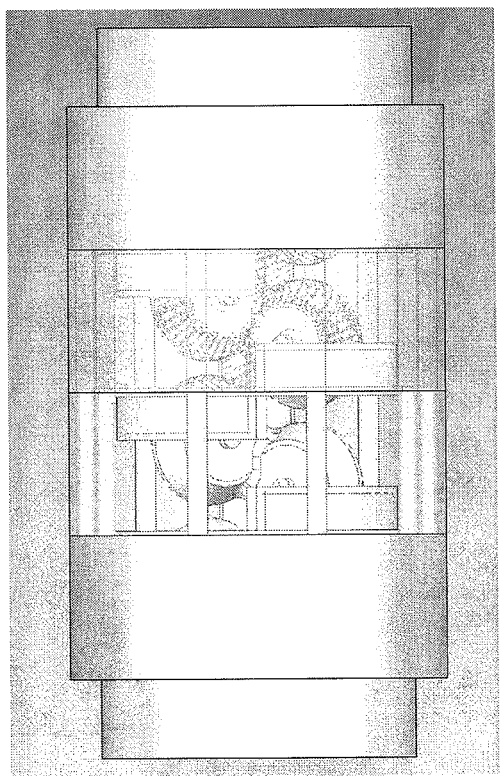
FIG. 16 is a view from the left of the mixer illustrated in FIG. 13.
Figure 17:
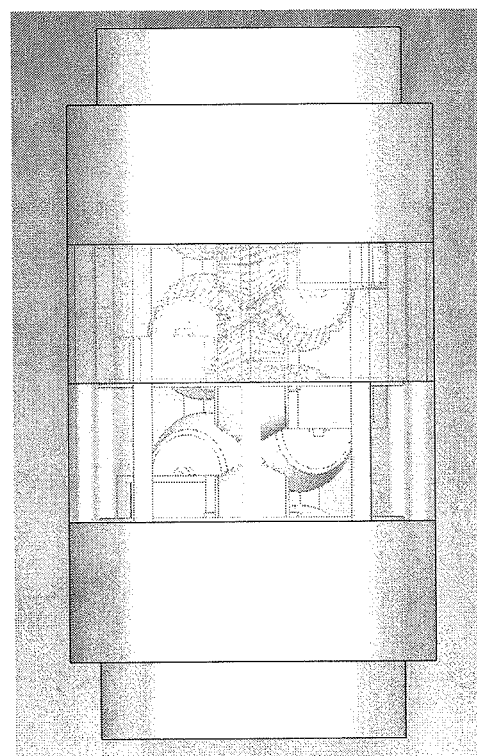
FIG. 17 is a view from the right of the mixer illustrated in FIG. 13.
Figure 18:
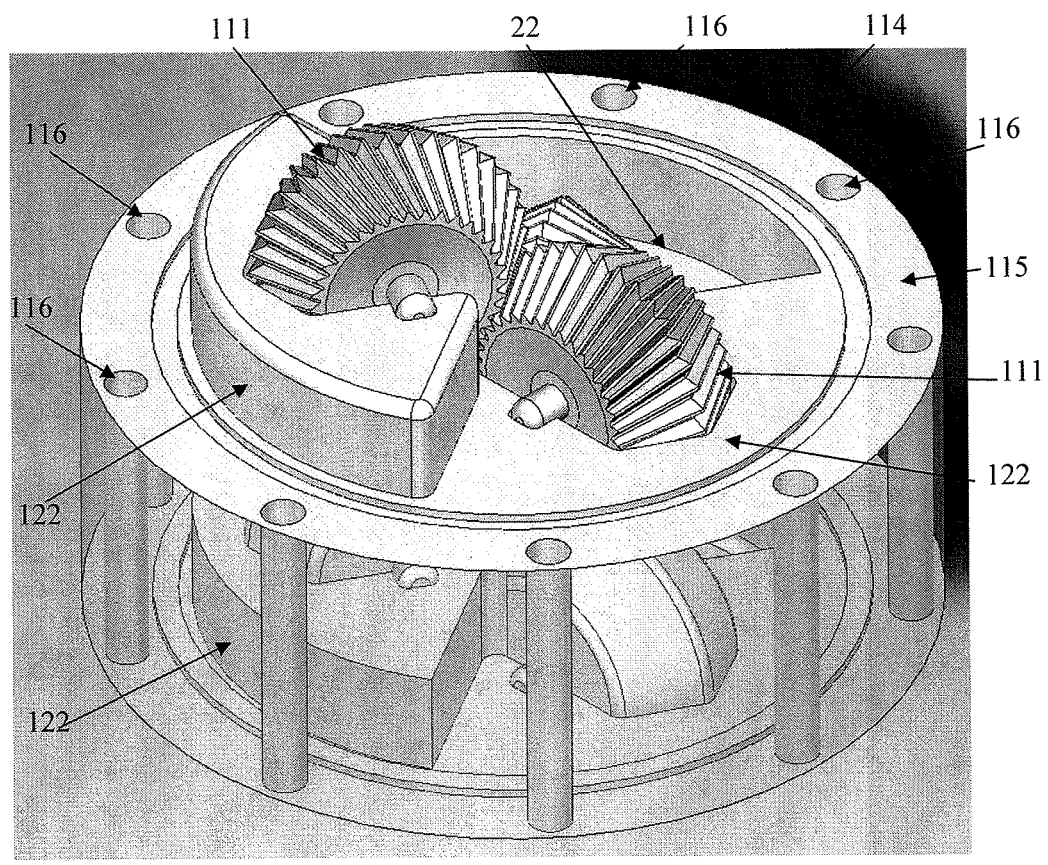
FIG. 18 is an isometric of an intermediate portion of a modular mixer according to a preferred embodiment of the present invention.
Figure 19:
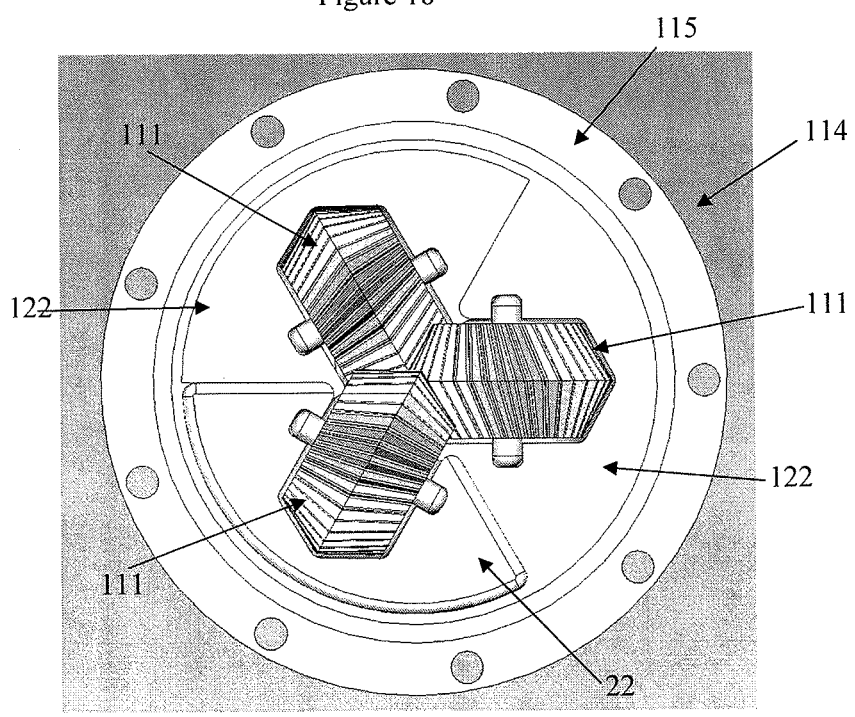
FIG. 19 is a view from below of the portion illustrated in FIG. 18.
Figure 20:
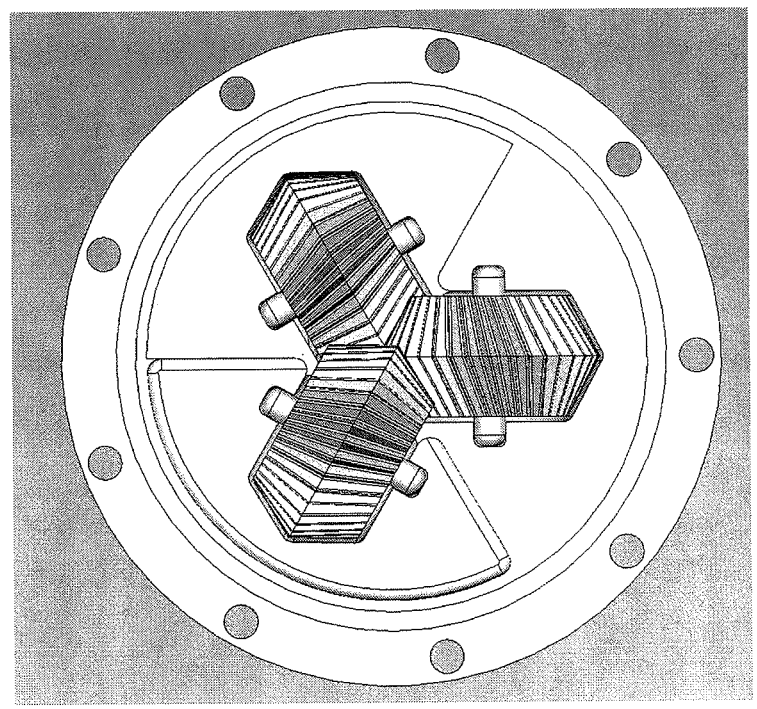
FIG. 20 is a view from above of the portion illustrated in FIG. 18.
Figure 21:
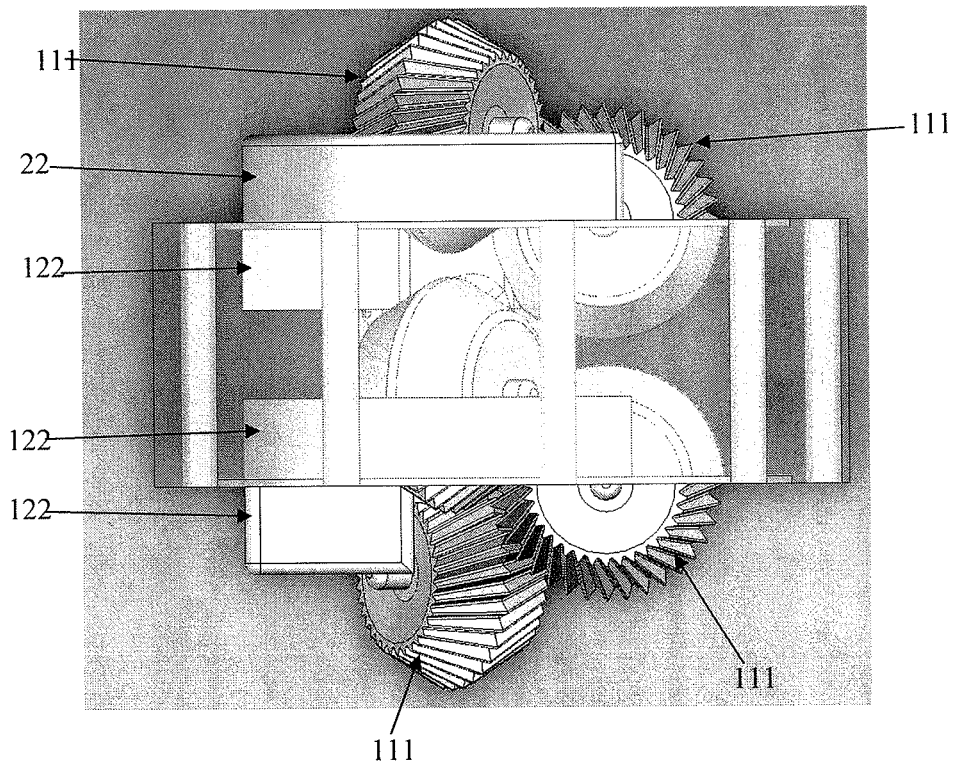
FIG. 21 is a view from the front of the portion illustrated in FIG. 18.
Figure 22:
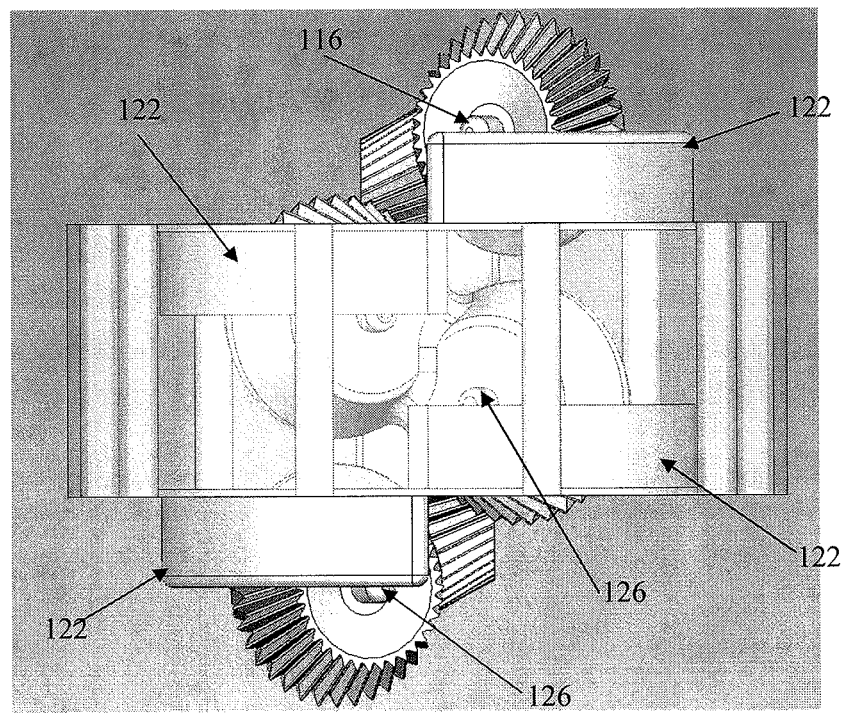
FIG. 22 is a view from the left of the portion illustrated in FIG. 18.
Figure 23:
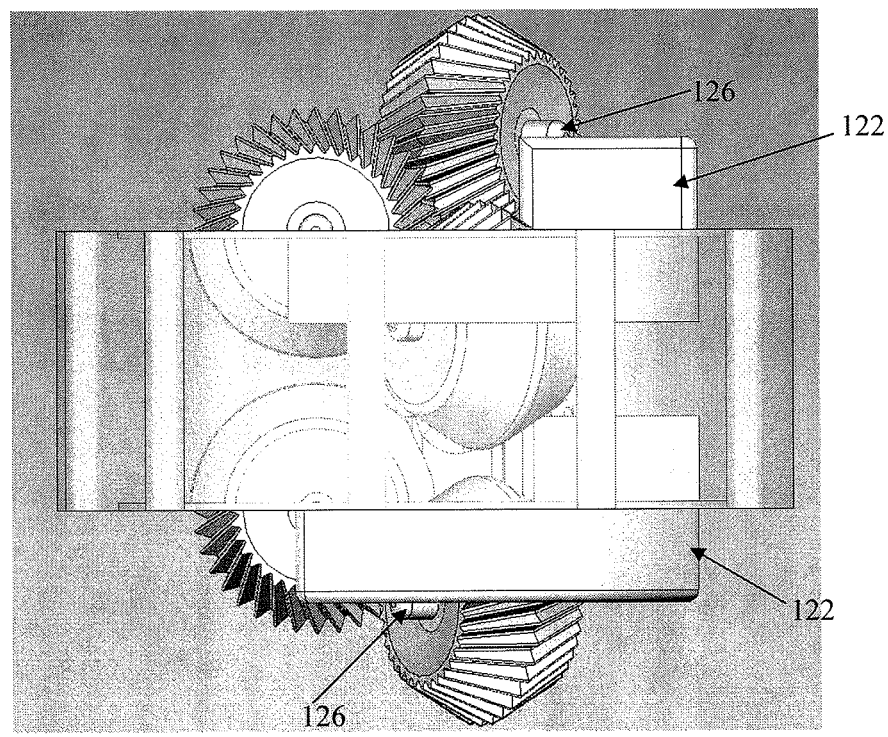
FIG. 23 is a view from the rear of the portion illustrated in FIG. 18.
Figure 24:
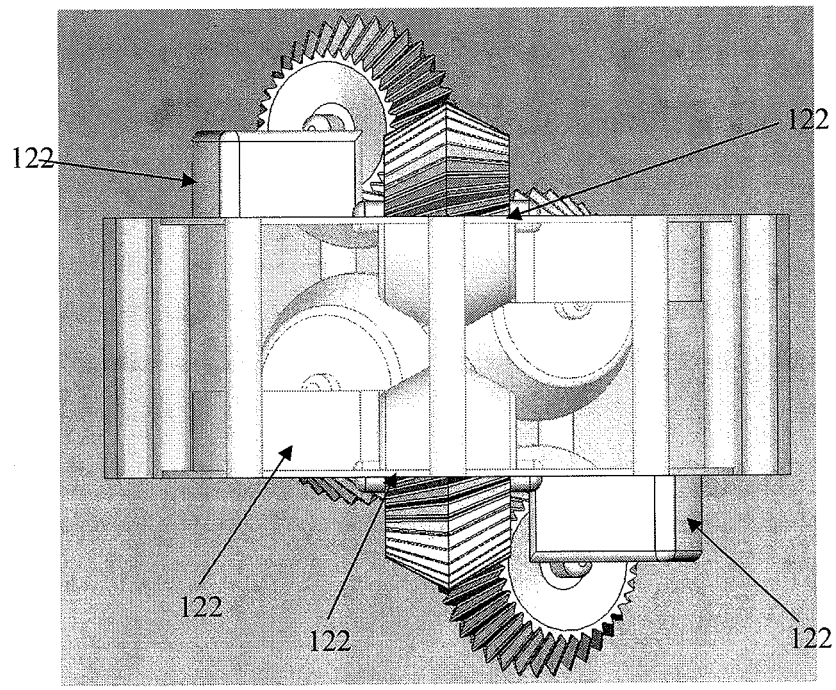
FIG. 24 is a view from the right of the portion illustrated in FIG. 18.
Figure 25:
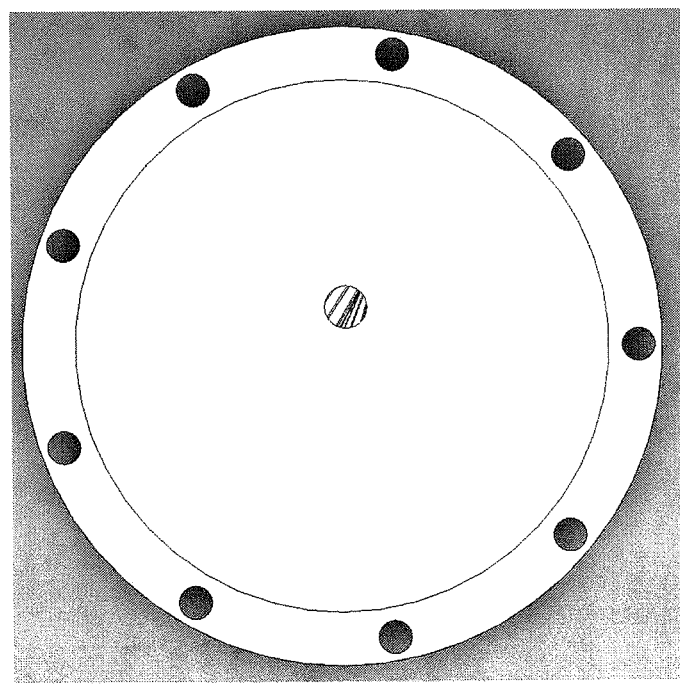
FIG. 25 is a view from the top of the mixer illustrated in FIG. 13 which is a mirror image of the bottom of the mixer.

As illustrated best in FIG. 12, a lower portion of the inner module 211 is thicker as is an upper portion of the inner module 211. The thicker lower portion of the inner module 211 extends from the waist 213 of the inner module, through the separation surface 214 portion and to the lip 215.

An upper portion of the inner module 211 is thicker as well. The upper portion extends from an upper section of the waist 213, across the shoulder 221 to the crown 212 forming an upper portion of the inner module 211 which is substantially solid except for the mixture inlet 216.

The inner module 211 is mounted for rotation about a central axis which is typically coaxial with a central axis of the mixture inlet 216. The tubular inlet 26 may be used as a mounting means in order to rotate the inner module 211. Rotation may be achieved using any mechanism or drive means to achieve the rotation.

As best illustrated in FIG. 12, the outer hood 217 is shaped to correspond to the shape of the inner module 11. In particular, an inner surface of the outer hood 217 is shaped to correspond to an outer shape of the inner module 211.

The inner surface of the outer hood 217 is spaced from the outer surface of the inner module 211 over its height with the separation distance between the inner surface of the outer hood 217 and the outer surface of the inner module 211 narrowing over the height of separator, towards the top of the separator 210. The separation distance between the hood 217 and the inner module 211 is larger at an upper portion of the separator 210 than at a lower portion of the separator.

The crown 212 of the inner module 211 is separated from the crown 220 of the outer hood 217.

According to the illustrated embodiment, a single vapour outlet 118 is provided approximately centrally across the crown 120 of the outer hood 117 and directly over the mixture inlet 116 of the inner module 111.

The outer hood 217 illustrated in FIG. 12 has a side wall which is thicker through the waist than the portions at the crown, adjacent the separation surface 14 of the inner module and at the lip.

As illustrated in FIG. 12, when the inner module 211 is fitted within the outer hood 217, an annular opening 222 is defined between the lip 215 of the inner module 211 and the lip of the hood 217 at a lower end of the separator 210. Liquid can exit through this annular opening 222 and the annular opening 222 will also allow air to enter the separator 210 in a direction opposite or substantially opposite to that of the mixture flow.

According to the embodiment of the present invention illustrated in FIGS. 1 to 3D, the biodiesel manufacturing apparatus includes a heated cauldron 99 for primary separation of glycerol from the process fluid located in the process stream after the mixer. The heated cauldron 99 is mounted above and immediately adjacent the hot oil tank 60. Also illustrated in this particular embodiment is a secondary settling tank 62 located in the process flow. This settling tank may be used for further separation of the FAME or bio diesel from other components remaining in the process flow. The chantrelle 95 (a preferred form of which is illustrated in FIGS. 7 to 12) for separation of excess alcohol from the process fluid through a differential pressure vaporisation process is mounted directed above and usually in fluid communication with the secondary settling tank 62 in the location illustrated.

The preferred embodiment illustrated in FIGS. 34 to 38 differs from that illustrated in FIGS. 1 to 3D in a number of ways but primarily in the provision of a combined reactor and primary separation vessel 61 and in the replacement of the chantrelle 95 and secondary settling tank 62 with a vacuum evaporation separation assembly 301.

The vacuum evaporation separation assembly 301 illustrated includes a secondary heater 302 and vacuum tower 303 for separation of excess alcohol from the process fluid through vaporisation under vacuum. A particularly preferred configuration for the secondary heater is illustrated in FIG. 33.

In operation, a fluid having at least one volatile component mixed therein enters through flows from the top of the sealed reactor tank into the secondary heater generally including a tube and a heating element. Once the secondary heater 302 is flooded, the re-heated fluid is fed continuously into the vacuum tower 303, which is located on the process side of the plant. A vacuum is preferably drawn throughout the tower 303 by a vacuum pump 304. Vapour is removed from the vacuum tower 303 through the vacuum pump 304 and overboard where it is preferably condensed at atmospheric pressure and stored externally to the plant. The fluid preferably flows over a series of dish-like trays stacked vertically within the tower 303. The fluid is then collected and pumped out of the bottom of the tower 303.

As illustrated in FIGS. 34 to 38, there may also be one or more filters located after the separation process steps in order to provide the biodiesel in as clean a form as is possible for the use. In this embodiment a pair of cellulose filters 305 and one polishing or finishing filter 306 are provided. The filters are illustrated in the embodiment illustrated in FIGS. 34 to 38, but not in the embodiment illustrated in FIGS. 1 to 3D. A similar configuration will however normally be provided in the embodiment illustrated in FIGS. 1 to 3D.

One more pumps 63 will be provided in association with the chemicals required for the esterification and trans-esterification reactants and/or the finished bio diesel in order to move the bio diesel to its required location. A finished biodiesel storage tank may be provided. The pumps are illustrated in the embodiment illustrated in FIGS. 1 to 3D as well as the embodiment illustrated in FIGS. 34 to 38.

Figure 34:
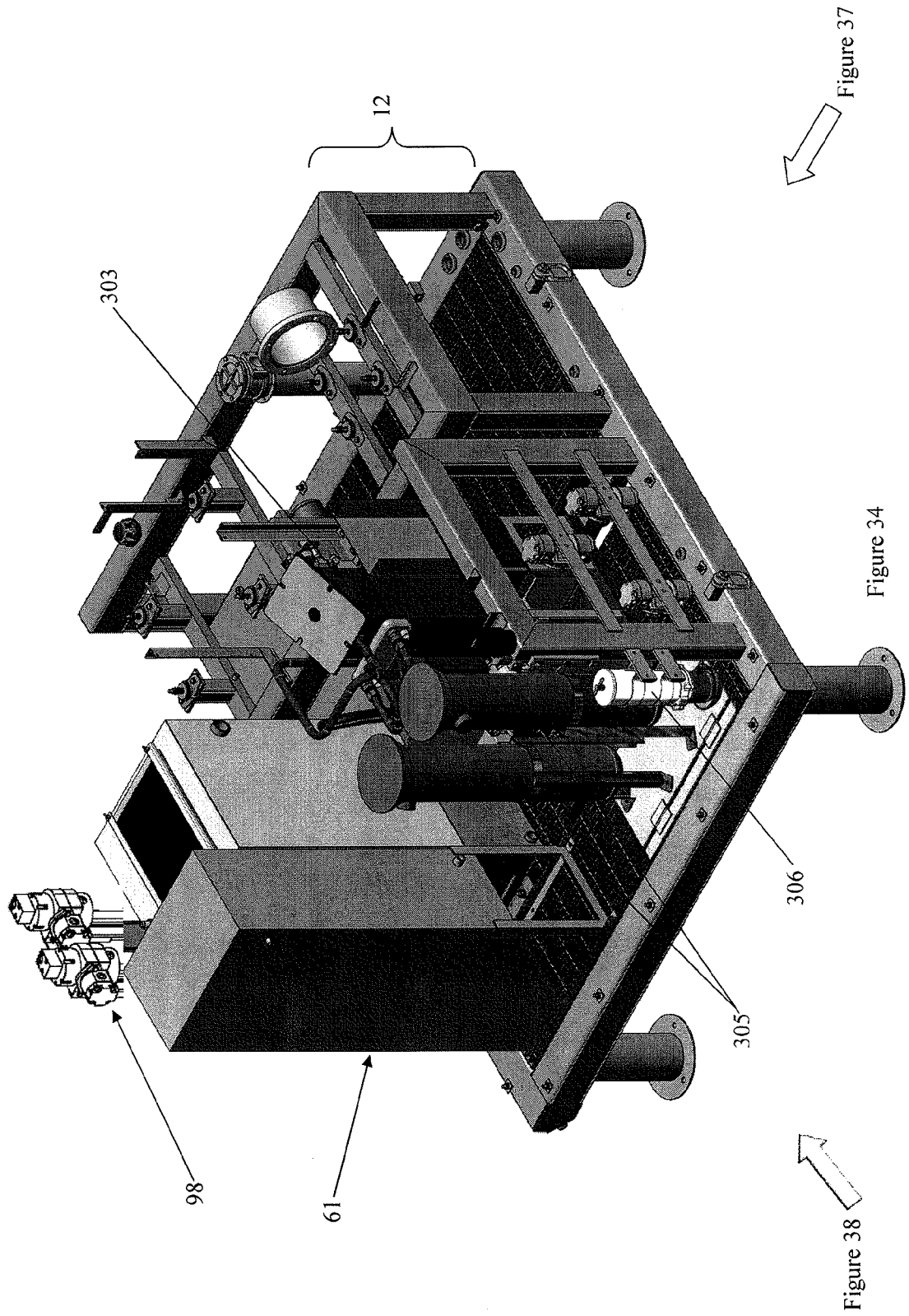
FIG. 34 is an isometric view from a first side of a further preferred embodiment of the biodiesel manufacturing apparatus.
Figure 35:
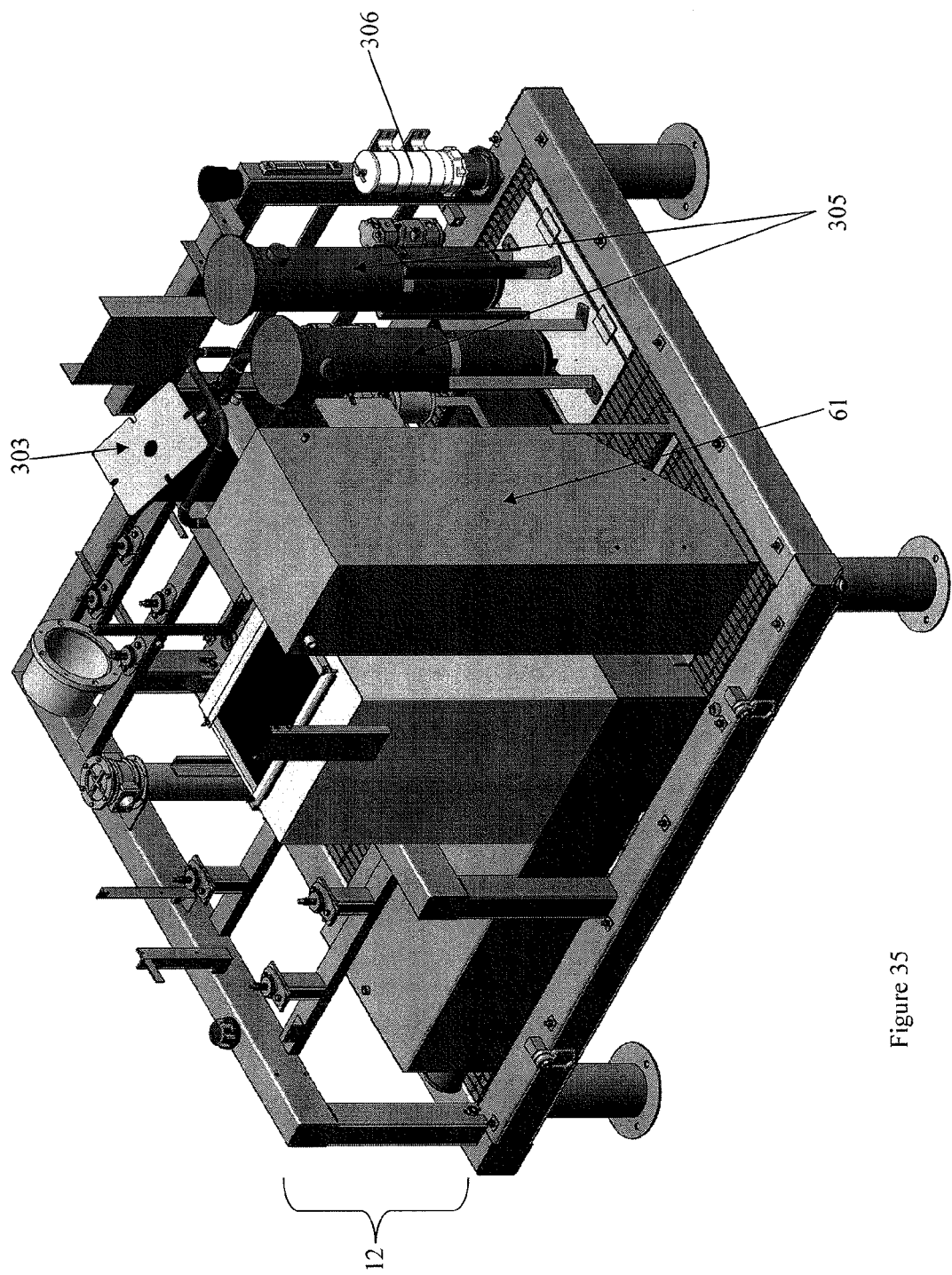
FIG. 35 is an isometric view from a second side of the biodiesel manufacturing apparatus illustrated in FIG. 34.
Figure 36:
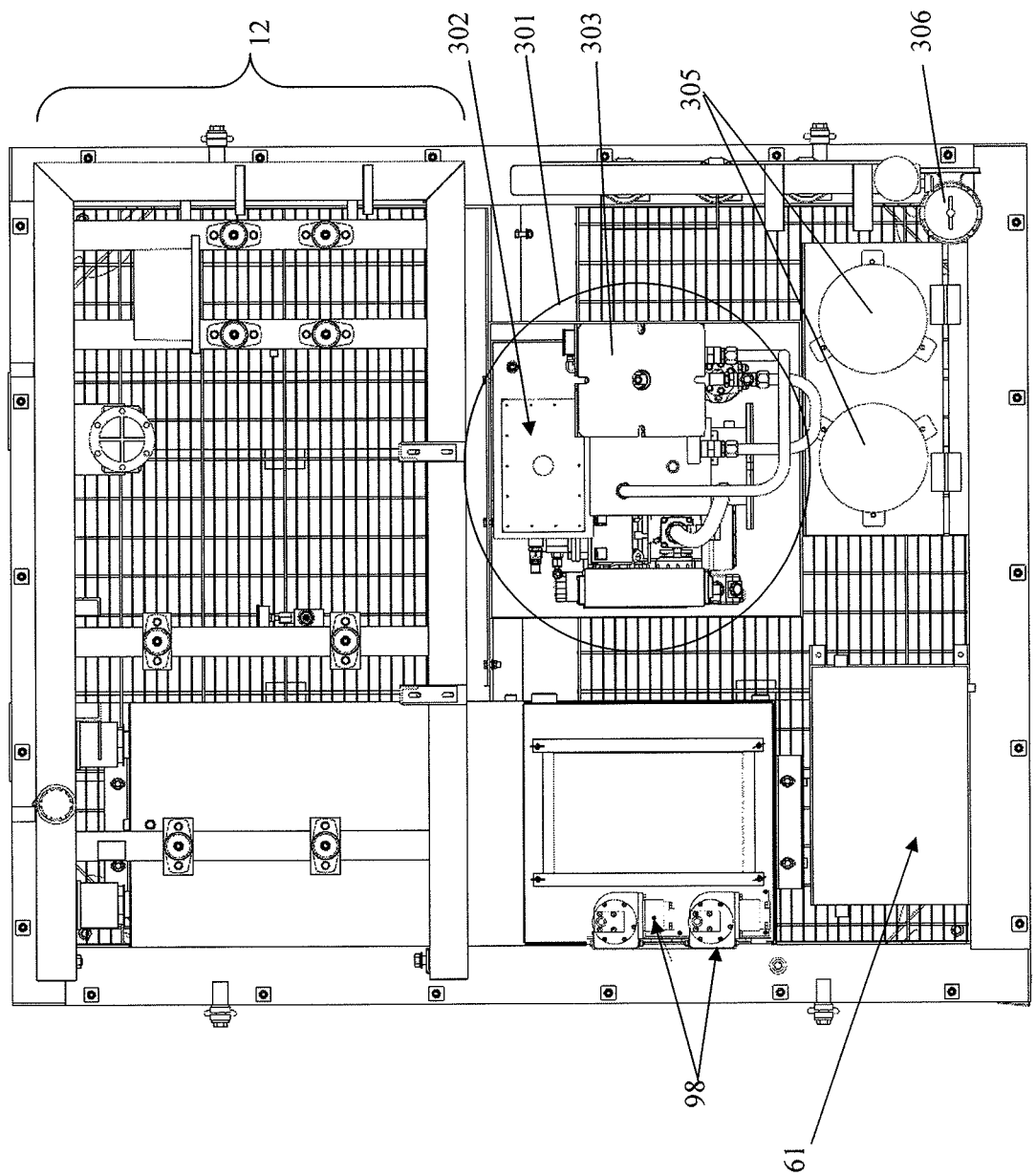
FIG. 36 is a plan view of the biodiesel manufacturing apparatus illustrated in FIG. 34.
Figure 37:
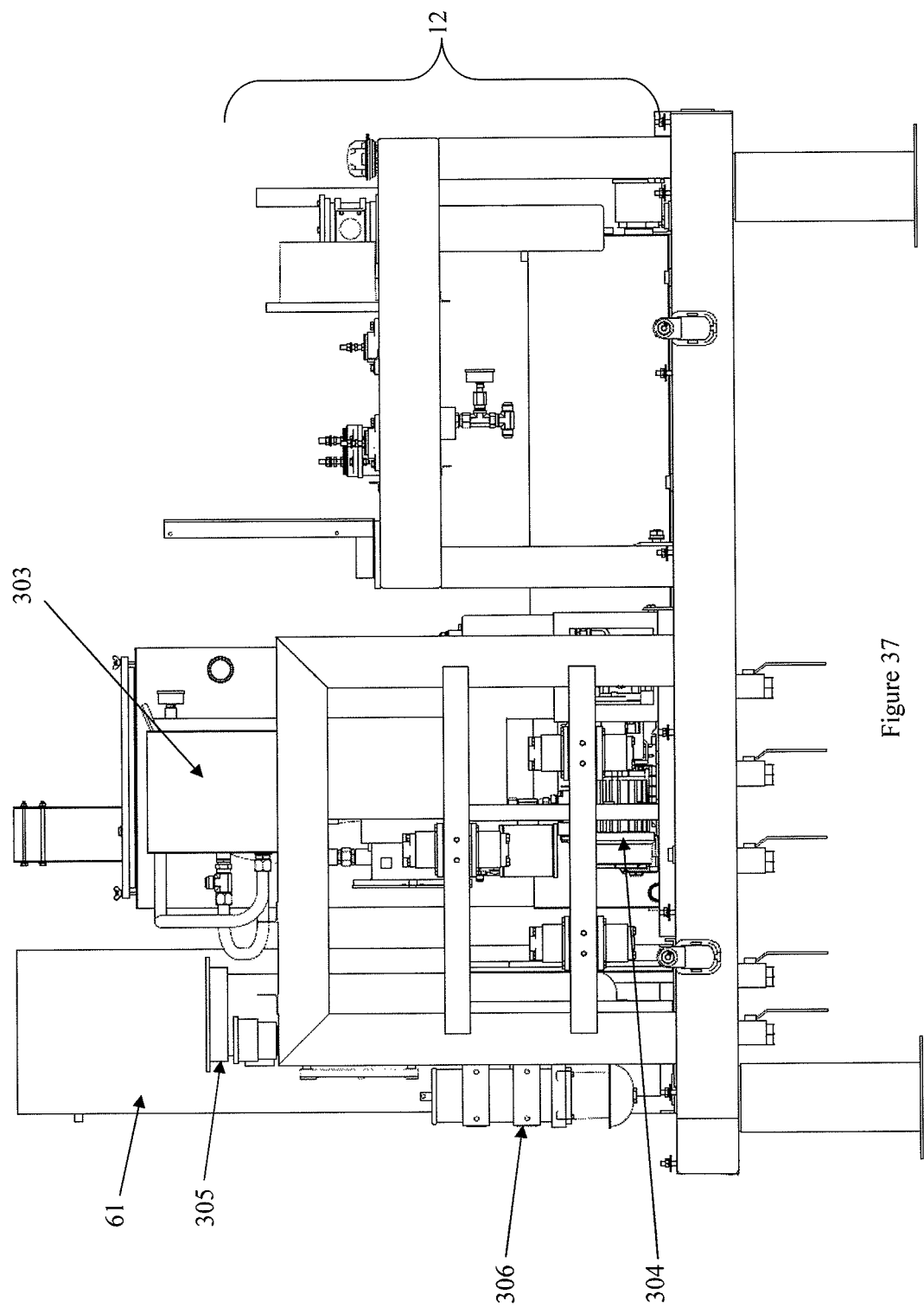
FIG. 37 is a side elevation view of the biodiesel manufacturing apparatus illustrated in FIG. 34 from the direction shown in FIG. 34.
Figure 38:
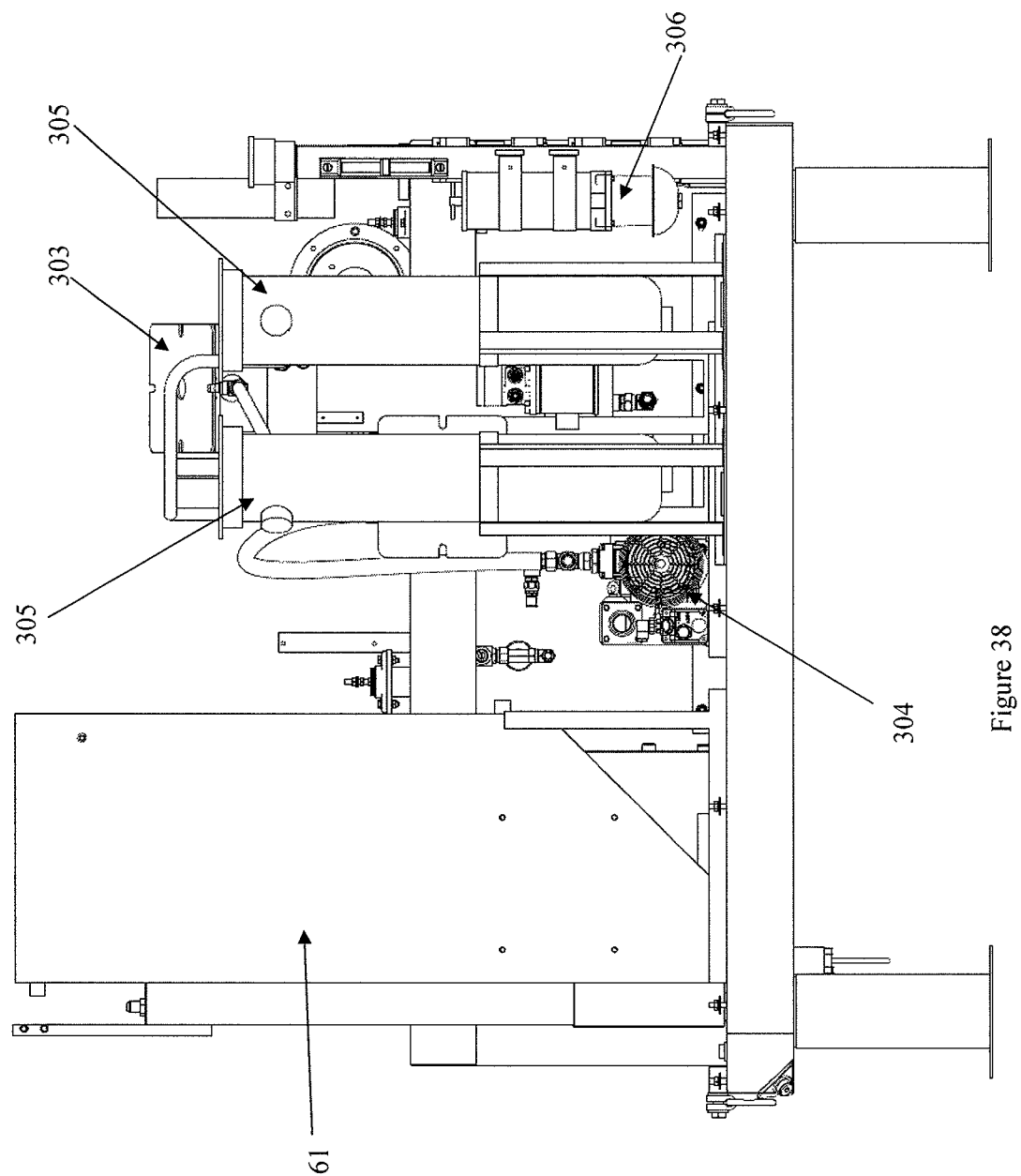
FIG. 38 is a side elevation view of the biodiesel manufacturing apparatus illustrated in FIG. 34 from the direction shown in FIG. 34.

Also illustrated in FIGS. 34 and 36 and located in a similar location in the embodiment illustrated in FIGS. 1 to 3D are a pair of mixers 98, normally one provided for alkali mixing and the other for acid mixing as required.

Electrical System

All electric motors to provide power to the pumps and the like are located outside the process area, in the power generation end of the housing. Control wiring and valve operating servos are low voltage with the cabling shielded and led to the control panel through a gas tight gland.

All lights and warning indicators are LED's or LCD's where appropriate. The control panel is located outside the process area.

Ventilation

Where possible, natural air flow is encouraged. The container itself is mounted on legs some 450 mm above a concrete plinth ensuring a natural flow of air under the machine encouraging the circulation of air within the process area.

Air from an engine driven cooling fan can be ducted and split to provide the necessary airflow to positively vent the methanol vapours and to provide a positive flow of ventilating air. As this fan is not driven by any electrical device, the risk of spark is eliminated.

Servicing

The servicing regime is minimal, however certain items are essential.

The engine manufacturer's recommendations are to be followed rigidly. Oil changes should be undertaken every 250 hours.

The coolant should be blended in accordance with the manufacturer's recommendations.

Filters on the oil feed from the expeller must be cleaned daily.

The zeolite column must be cleaned daily, and replaced every 10,000 liters.

The filter elements in the polishing system must be cleaned every day.

The oil tank should be drained of any condensation or water prior to starting every morning.

The fuel holding tank should be drained of moisture daily.

Installation on Site

It is recommended that, where possible, the plant of the present invention is mounted on a level, hard foundation, not less than 4 meters×4 meters. Within the square a hollow section is excavated, approximately 2.5 meters×2 meters×0.5 meters. The excavated section should be completely filled to its maximum depth with Zeolite for containment of spills and to reduce noise.

There is a considerable amount of traffic around a plant of the present invention: the movement of chemicals, the movement of finished product and the movement of people. The products of the process and the chemicals used in the process are dangerous and can cause serious injury if mishandled. It is imperative that the recommendations of the distributor are fully considered and applied rigorously.

In operation, there is always a risk of fire, so smoking in the vicinity of 15 meters of the plant of the present invention is absolutely forbidden.

When the plant of the present invention is delivered, an earthing or grounding rod should be driven firmly into the ground. The container's feet will be delivered loose.

When the plant of the present invention is lifted from the truck—it weighs approximately 2,700 kgs upon delivery—the container should first be rested in its approximate position on trestles (supplied by the distributor for this stage of the installation). The feet should be firmly attached to the bottom frame.

The plant of the present invention should be placed in position and the holes in the feet marked on the solid base. The container is removed to permit access to drill the locating bolts, which will be either chemical anchors or expanding bolts.

The plant of the present invention will be swung into position

After checking that the machine is adjusted for level by shimming the feet, it can be secured to the base.

The earth or ground strap terminals should be checked for tightness, and the cable secured under the machine.

The plant may include a preliminary step of an esterification sub-process including a reactor in which the process fluid is reacted with alcohol via selective esterification by a catalyst before the trans-esterification process.

This esterification sub-process may be provided in a separate module that is connectable in line with the raw oil lines from the source. Normally, if the esterification module is provided, the raw oil will proceed through that process prior to the trans-esterification process. The raw oil will normally be heated in a raw oil heating tank, normally a heat exchanger. The heat exchanger will preferably supply enough energy to the oil to raise the raw oil temperature to approximately 45° C.

The esterification sub-process will likely include an acid resin dosing mechanism to dose the process fluid in the presence of an alcohol. Suitable process equipment will be provided in the optional esterification module the plant to facilitate this sub-process.

If the process fluid is to be subjected to the esterification sub-process, it will typically undergo esterification after primary heating. A filter will usually be used to filter the raw oil prior to heating in the preferred hot oil tank and a second filter after heating in the hot oil tank.

The esterification sub process will normally involve reacting a mixture of free fatty acids in the process fluid with alcohol via selective esterification by a catalyst that selectively esterifies the desired free fatty acid(s). A preferred catalyst for this purpose is Amberlyst BD-20 by Rohm and Haas.

A flow reactor 30 or a portion of a flow reactor located in a column may be used in a preferred embodiment with a separation tank associated therewith in which water is separated from the esterification reaction mixture. Preferably, the reactor 30 is configured as a co-current flow reactor, i.e., the fatty acid and alcohol pass through the reactor in the same direction. An alcohol pump 31 can be provided for dosing the alcohol into the reactor 30.

Typically, the product stream from the reactor is sent to a transesterification process, where it is contacted with a transesterification catalyst and an alcohol, preferably after separating as much of the water as possible. A tank is typically provided for separation of the water. An evaporator may also be provided to recover unused alcohol.

Typically, the esterification reaction is carried out in a flow reactor 30, and preferably the contact time is at least 30 minutes, alternatively at least 45 minutes. Preferably, the contact time is no more than 6 hours, alternatively no more than 4 hours, alternatively no more than 2 hours.

The residence time in the esterification system typically will be dependent upon required production output and will typically be determined according to the maximum production output. It may also be dependent upon the particular raw oil feedstock.

Preferably the catalyst is a gel-type acidic ion exchange resin having 0.25 wt % to 2.75 wt % crosslinker, and having sulfonic acid functionality. The reaction mixture is preferably in contact with the catalyst in a continuous reactor in a temperature range from 40° C. to 120° C. for at least 15 minutes.

The alcohol used will preferably be methanol or ethanol or another alcohol could be used in the esterification sub process.

The esterification sub process equipment may be provided in the plant of the present invention but the process may not be included in the process, dependent upon the feedstock used and in particular, the acid number of the raw oil feedstock. Alternatively and more preferred, the esterification sub-process will be provided as separate but attachable module for integration into the plant of the present invention if required.

If the esterification subprocess equipment is present in the plant, a bypass may be provided once the heating of the raw oil has been achieved. The bypass will typically connect more or less directly to the trans-esterification sub process. Typically however the esterification sub process may be used, at least to some extent, for most types of raw oil feedstock.

In use, there will be a number of operational procedures that an operator will follow in order to start, run and shut down the plant of the preferred embodiment. It is convenient to discuss each of these procedures in order of occurrence.

Pre Start Check

Normally, the first step in the start procedure is to ensure that the emergency stop activation buttons are reset. Further, the fuel level to operate the power generation means in order to run the process equipment should also be checked prior to start. The hydraulic oil level is also on the restart checklist. If the plant is being started from cold, the oil line may only be visible when the hydraulic oil has been heated to a suitable level. If still not visible when the hydraulic oil is warm, then additional hydraulic oil will be required. It is also recommended that the operator check the levels and connections of process chemicals that are used in the transesterification and/or esterification reactions and any other process chemicals that may be required.

Finally, a check of all of the connections and the conduits between the various components of the plant should be undertaken in order to ensure that they are unobstructed and that there are no leaks in any of the conduits and that all of the valves and connectors are in the correct position to allow flow as required.

All of the drain valves should be checked to ensure that they are closed.

Next, the fuel filter is typically primed and the lift pump to provide the fuel to be engine is also normally primed. The electrical connectors are then turned to the start position.

Operation Procedure

Once the electrical connectors are turned to the start position, the engine governor switch is placed in the idle position. The ignition for the engine is typically a key cylinder similar to a vehicle ignition with an electric start. Once the key has been turned on the engine has started, the engine should be allowed to idle for approximately 5 minutes after which time the engine governor switch can be moved to the run position. Once the engine is running, the raw oil pump is typically activated and once the raw oil is above the heater level, the heating process is typically started. Once the level gauge in the hot oil tank is full, the raw oil pump can be turned off.

The heating process for heating the oil should heat the oil to approximately 108° C. The heating process may require one or more periods of heating as the heating process is typically timed. A display, typically light will signal when the required temperature in the oil has been reached. The heating process also has a high level cut-off switch which deactivates the heaters when the oil temperature reaches the preferred 108° C.

The mixer is then typically activated followed shortly thereafter by activation of the chemical pump switches and then the hot oil pump which provide the required chemicals and hot raw oil to the mixer. Once the hot oil level begins to drop as indicated on a display, the raw oil pump is typically turned back on and left on while the plant is operating.

Once the chemical pumps are active, the flow through the chemical pumps should be monitored to ensure that the flow rate is correct. After a period of operation, the settling tank will fill and once a required level is reached, typically approximately 100 millimeters from the top of the settling tank, the biodiesel pump can be activated.

Biodiesel will then begin to flow from the settling tank and into the preferred filtration stages. Normally, the filters will require venting in order to remove air which may have accumulated in the filters and in order to prevent backflow. Bleed valves are typically provided at an upper portion of the filter vessels and the bleed valves normally opened until biodiesel begins to flow out the bleed valve and then they are closed. This will normally take place in one or more filters successively in order.

The filtered biodiesel will then flow from the final, washing filter for use. The finished biodiesel may be collected in an IBC or used for directly without storage.

Shutdown Procedure in order to shut down the plant, the raw oil pump is typically turned off first. The hot oil pump is typically of an deactivated followed by the chemical pumps. The mixer motor is then deactivated followed by closing off of the hot oil valve. Once these steps have been performed, the engine can be deactivated, normally by moving the governor switch to idle and then off and the electrical isolation switch can be turned off.

Emergency Stop Procedure

According to the emergency stop procedure, at least one cutout switch will be provided which, when activated, will normally shut down the entire plant. This typically occurs by disconnecting the electrical power. At this stage, the reason for the emergency stop procedure is typically identified and corrected if required before attempting restart.

In order to restart the plant, the emergency stop switches will need to be reset. Normally, the pre-start checklist will then be followed which resets all of the process and power generation equipment to the required start position.

There is also a maintenance procedure that should be followed with the plant of the preferred embodiment. The number of the features of the plant of the preferred embodiment will require some maintenance. Typically, regular cleaning and draining of the settling tank will be required as will cleaning of the filters. In particular, the final biodiesel polishing filter should be cleaned or at least checked on a daily basis.

The engine fuel filter should also be checked regularly, typically on a daily basis as will any filter that is provided from the chemical store.

The other filters can be checked on a weekly basis and engine oil filter is typically checked every 1000 hours. The pressure gauges in flow meters in relation to the raw oil and hot oil in particular should be checked on a daily basis to ensure proper positioning.

In the present specification and claims (if any), the word "comprising" and its derivatives including "comprises" and "comprise" include each of the stated integers but does not exclude the inclusion of one or more further integers.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more combinations.

The invention claimed is:

1. A transportable biodiesel manufacturing or processing plant for processing on continuous basis, a process fluid from a raw oil feedstock, the plant including
   (a) an external housing containing power generation equipment,
   (b) an inlet for raw oil from an oil bearing plant crop or waste plant based oil, and
   (c) process equipment including
      i. a raw oil heating vessel for heating the raw oil prior to mixing,
      ii. a powered high-shear mixer to mix triglycerides from the raw oil, and at least one reactant alcohol according to a transesterification process mixing occurring after the raw oil has been heated, to form a process fluid, the powered high-shear mixer including an outer housing having a central longitudinal axis, at least two interengaging, counter-rotating toothed mixing bodies, the toothed mixing bodies each rotating about a central axis, the respective axes offset radially and spaced along the central longitudinal axis of the outer housing,
      iii. a heated combined reactor and primary separation/settling tank for the continued reaction of the triglycerides and at least one alcohol to produce at least one fatty acid ester and at least one alcohol, from which one or more products is withdrawn to drive the transesterification process to higher conversion;
      iv. a heater and vacuum separator for separation of the at least one alcohol from the at least one fatty acid ester through drawing of a vacuum over the heated process fluid and vaporisation process, and
      v. one or more finishing processes.

2. A biodiesel manufacturing or processing plant as claimed in claim 1 wherein the transesterification reaction uses raw oil and a supercritical alcohol, at a high temperature and pressure in a continuous process.

3. A biodiesel manufacturing or processing plant as claimed in claim 1 wherein the plant includes a frame assembly to which process equipment for the biodiesel manufacturing is mounted and relative to which the external housing is mounted to house the plant.

4. A biodiesel manufacturing or processing plant as claimed in claim 3 wherein the housing is divided into two compartments namely a first compartment containing the power generation equipment to provide power and a second compartment housing process equipment with the power generation equipment providing power to operate the process equipment.

5. A biodiesel manufacturing or processing plant as claimed in claim 1 wherein the combined reactor and primary separation tank/settling tank is provided with a residence time optimised to allow at least a transesterification reaction to occur and at least partial separation of products formed in the transesterification reaction.

6. A biodiesel manufacturing or processing plant as claimed in claim 5 wherein the combined reactor and primary separation tank/settling tank is provided with at least one outlet to draw off at least one product formed in the transesterification reaction in order to drive equilibrium of the transesterification reaction toward the products.

7. A biodiesel manufacturing or processing plant as claimed in claim 1 wherein the heater and vacuum separator is provided with a vacuum applied thereto at an elevated temperature in order to separate more volatile components.

8. A biodiesel manufacturing or processing plant as claimed in claim 1 wherein the plant includes a separate module, which is provided in association with the plant in order to submit the raw oil to an esterification reaction before the transesterification reaction.

9. A biodiesel manufacturing or processing plant as claimed in claim 1 wherein the outer housing has at least a pair of end portions, each end portion having at least one toothed mixing body, the toothed mixing bodies of the respective end portions interengaging and counter-rotating about a central axis, the respective axes offset radially and spaced along the central longitudinal axis of the outer housing.

10. A biodiesel manufacturing or processing plant as claimed in claim 1 wherein the outer housing has at least a pair of end portions and at least one intermediate portion, each of the at least a pair of end portions and at least one intermediate portion having at least one toothed mixing body, the toothed mixing bodies of the respective portions interengaging and counter-rotating about a central axis, the respective axes offset radially and spaced along the central longitudinal axis of the outer housing.

11. A biodiesel manufacturing or processing plant as claimed in claim 1 wherein the mixer is a high-shear mixer with one or more high-energetic shear zone to allow a reaction to begin to take place in the mixer by reducing the droplet size of immiscible liquids.

12. A biodiesel manufacturing or processing plant as claimed in claim 1 including an esterification subprocess including a reactor in which the process fluid is reacted with alcohol via selective esterification by a catalyst, prior to the transesterification process.

\* \* \* \* \*